United States Patent
Kim et al.

(10) Patent No.: US 9,556,454 B2
(45) Date of Patent: Jan. 31, 2017

(54) GENERATION OF INDUCED PLURIPOTENT STEM (IPS) CELLS

(71) Applicant: Max-Planck-Gesellschaft zur Foerderung der Wissenschaften e.V., Munich (DE)

(72) Inventors: Jeong Beom Kim, Münster (DE); Holm Zaehres, Mülheim/Ruhr (DE); Hans Robert Schöler, Münster (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 14/692,250

(22) Filed: Apr. 21, 2015

(65) Prior Publication Data

US 2015/0218585 A1 Aug. 6, 2015

Related U.S. Application Data

(63) Continuation of application No. 12/993,890, filed as application No. PCT/EP2009/003735 on May 26, 2009, now abandoned.

(60) Provisional application No. 61/166,689, filed on Apr. 3, 2009.

(30) Foreign Application Priority Data

May 27, 2008 (EP) .................................. 08009651

(51) Int. Cl.
| | |
|---|---|
| *C12N 15/00* | (2006.01) |
| *C12N 15/85* | (2006.01) |
| *C12N 5/074* | (2010.01) |
| *C12N 15/873* | (2010.01) |
| *A61D 19/04* | (2006.01) |

(52) U.S. Cl.
CPC ........... *C12N 15/8509* (2013.01); *A61D 19/04* (2013.01); *C12N 5/0696* (2013.01); *C12N 15/85* (2013.01); *C12N 15/873* (2013.01); *C12N 2501/602* (2013.01); *C12N 2501/603* (2013.01); *C12N 2501/604* (2013.01); *C12N 2501/606* (2013.01); *C12N 2502/13* (2013.01); *C12N 2506/13* (2013.01); *C12N 2510/00* (2013.01); *C12N 2799/027* (2013.01)

(58) Field of Classification Search
USPC ................................................. 435/325, 455
See application file for complete search history.

(56) References Cited

U.S. PATENT DOCUMENTS

| | | | | |
|---|---|---|---|---|
| 8,071,369 | B2 * | 12/2011 | Jaenisch ................ | C12N 15/85 435/325 |
| 8,298,825 | B1 * | 10/2012 | Hochedlinger ...... | C12N 5/0696 435/325 |
| 2007/0264232 | A1 * | 11/2007 | Ho ....................... | C12N 5/0623 424/93.1 |

FOREIGN PATENT DOCUMENTS

| | | |
|---|---|---|
| JP | 2002-511248 | 4/2002 |
| WO | 99/53028 A1 | 10/1999 |
| WO | 2007/069666 A1 | 6/2007 |

OTHER PUBLICATIONS

Thomson (1995, PNAS, vol. 92, pp. 7844-7848).*
Zappone (Development, 2000, vol. 127, p. 2367-2382).*
Takahashi (Cell, 2006, vol. 126:663-676).*
Okita (Nature, Jul. 19, 2007, vol. 448, p. 313-317).*
Yu (Science, Nov. 20, 2007, vol. 318, p. 1917-1920).*
Meissner (Nature Biotechnology, Aug. 27, 2007, vol. 25: 1177-1181).*
Blelloch (Cell Stem Cell, Sep. 13, 2007, vol. 1, p. 245-247).*
Brambrink (Cell Stem Cell, Feb. 7, 2008, vol. 2, No. 2, p. 151-159).*
Nakagawa (Nat Biotechnol, 2008, vol. 26: 101-106).*
Duinsbergen (Experimental Cell Res. Jul. 9, 2008, vol. 314, p. 3255-3263).*
Eminli (Stem Cells, Jul. 17, 2008, vol. 26, p. 2467-2474).*
Kim (Nature, Jul. 2008, vol. 454, No. 7204, p. 646).*
Aasen (Nature Biotech., Nov. 2008, vol. 26, No. 11, p. 1276-1284).*
Loh (Blood, May 28, 2009, vol. 113, No. 22, p. 5476-5479).*

(Continued)

*Primary Examiner* — Michael Wilson
(74) *Attorney, Agent, or Firm* — DT Ward, PC; Donna T. Ward; Lingyun Jia

(57) ABSTRACT

The present invention relates to a method of generating an induced pluripotent stem (iPS) cell comprising the step of introducing into a target cell one or two coding sequences each giving rise upon transcription to a factor that contributes to the reprogramming of said target cell into an induced pluripotent stem cell and selected from Oct3/4 or a factor belonging to the Myc, Klf and Sox families of factors, wherein the target cell endogenously expresses at least the factors that are not encoded by the coding sequences to be introduced and selected from Oct3/4 or factors belonging to the Myc, Klf and Sox families of factors, and wherein the cell resulting from the introduction of the one or two coding sequences expresses the combination of factor Oct3/4 and at least one factor of each family of factors selected from the group of Myc, Klf and Sox. Furthermore, the present invention relates to an induced pluripotent stem cell generated by the method of the invention and a method of identifying a compound that contributes to the reprogramming of a target cell into an induced pluripotent stem cell. Also, a method of generating a transgenic non-human animal and a composition comprising an iPS cell generated by the method of the present invention for gene therapy, regenerative medicine, cell therapy or drug screening are envisaged.

2 Claims, 8 Drawing Sheets

(56) References Cited

OTHER PUBLICATIONS

Figure 1:
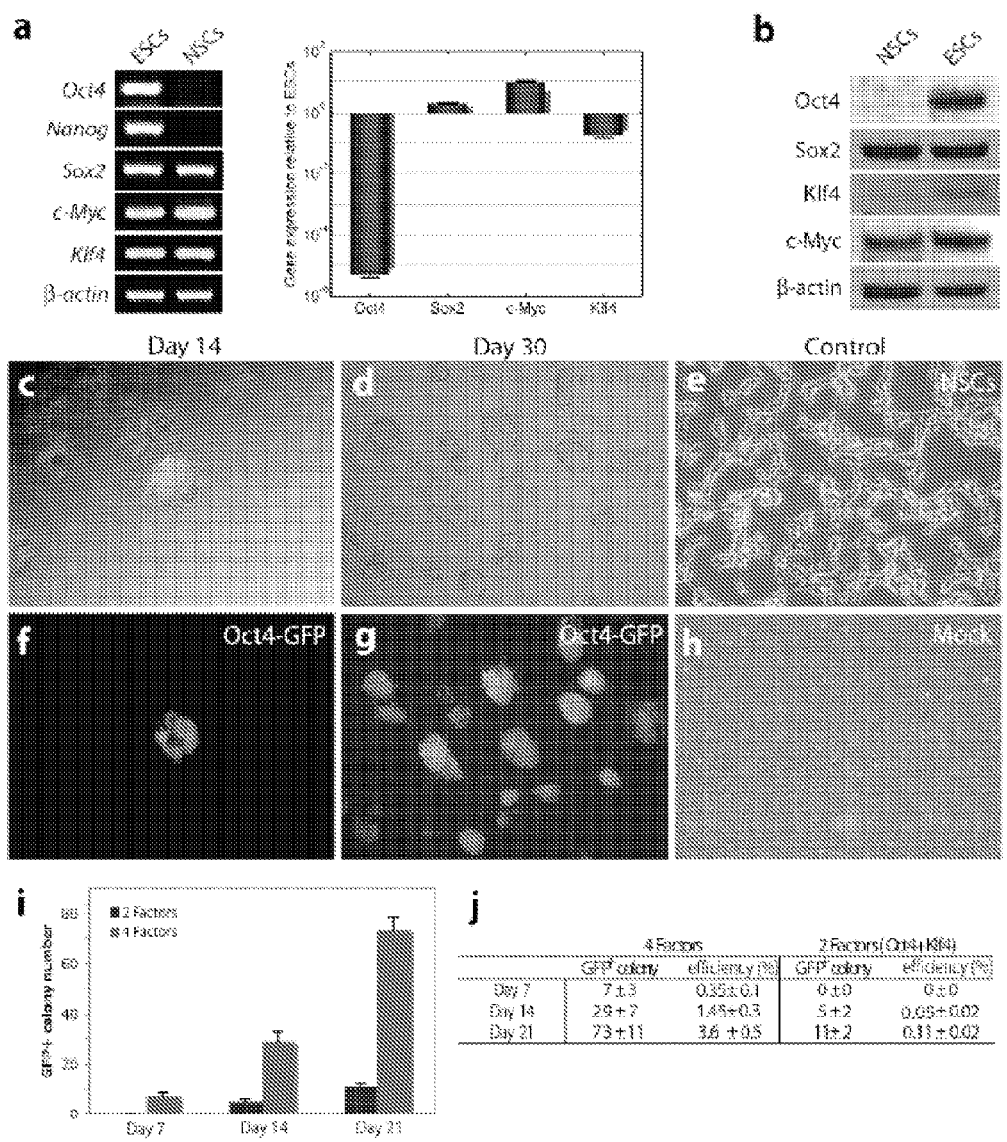

Kim (Cell, Feb. 6, 2009, vol. 136, p. 411-419).*
Patel (Stem Cell Rev. Sep. 2010, vol. 6, No. 3, p. 367-380).*
Kim, Jeong Beom et al., "Pluripotent Stem Cells Induced from Adult Neural Stem Cells by Reprogramming with Two Factors", Nature (London), Jul. 2008, pp. 646, vol. 454, No. 7204, XP002499568.
Kim, Jeong Beom et al., "Oct4-Induced Pluripotency in Adult Neural Stem Cells", Cell, Feb. 2009, pp. 411-419, vol. 136, No. 3, XP002525539701.
Do, Jeong Tae et al., "Nuclei of Embryonic Stem Cells Reprogram Somatic Cells", Stem Cells, Jan. 1, 2004, pp. 941-949, vol. 22, No. 6, Alphamed Press, Dayton, OH, US, XP002408190.
Do, Jeong Tae et al., "Comparison of neurosphere cells with cumulus cells after fusion with embryonic stem cells: reprogramming potential", Reproduction, Fertility and Development, Jan. 1, 2005, pp. 143-149, vol. 17, No. 102, CSIRO, East Melbourne, AU, XP009079885.
Nakagawa, Masato et al., "Generation of induced pluripotent stem cells without Myc from mouse and human fibroblasts", Nature Biotechnology, Jan. 2008, pp. 101-106, vol. 26, No. 1, Laser Focus World, Pennwell, Tulsa, OK, US, XP009098334.
Talahashi, Kazutoshi et al., "Induction of Pluripotent Stem Cells from Adult Human Fibroblasts by Defined Factors", Cell, Nov. 30, 2007, pp. 861-872, vol. 131, No. 5, Cell Press, Cambridge, MA, US, XP002478584.
Park, In-Hyun et al., "Reprogramming of human somatic cells to pluripotency with defined factors", Nature, Dec. 23, 2007, pp. 141-147, vol. 451, No. 7175, Nature Publishing Group, London, UK, XP002475655.
Takahashi, Kazutoshi et al., "Induction of pluripotent stem cells from fibroblast cultures", Nature Protocols, Jan. 1, 2007, pp. 3081-3089, vol. 2, No. 12, Nature Publishing Group, UK, XP001537991.
Hacein-Bey-Abina, S. et al., (2003) LM02-Associated Clonal T Cell Proliferation in Two Patients after Gene Therapy for SCID-X1, Science 302:415-419.
Ingvarsson, S. et al., (1988) Structure and Expression of B-myc, a New Member of the myc Gene Family, Molecular and Cellular Biology 8(8):3168-3174.
Kim, K et al., (2010) Epigenetic memory in induced pluripotent stem cells, Nature 467:285-292.
Kim, K. et al., (2011) Donor cell type can influence the epigenome and differentiation potential of human induced pluripotent stem cells, Nature Biotechnology 29:1117-1119.
Lister, R. et al., (2011) Hotspots of aberrant epigenomic reprogramming in human induced pluripotent stem cells, Nature 471:68-75.
Miyagi, S. et al., (2006) Sox2 as a self-renewal regulator of stem cells, Chiba Medical Journal 82(1):1-7.
Park, I.-H. et al., (2008) Generation of human-induced pluripotent stem cells, Nature Protocols 3(7):1180-1187.
Schepers, G. E. et al., (2002) Twenty Pairs of Sox: Extent, Homology, and Nomenclature of the Mouse and Human Sox Transcription Factor Gene Families, Development Cell 3:167-170.
Vennstrom, B. et al., (1982) Isolation and Characterization of c-myc, a Cellular Homolog of the Oncogene (v-myc) of Avian Myelocytomatosis Virus Strain 29, Journal of Virology 42(3):773-779.
Van Vliet, J. et al., (2006) Human KLF17 is a new member of the Sp/KLF family of transcription factors, Genomics 87:474-482.
Yamanaka, S., (2007) Strategies and New Developments in the Generation of Patient-Specific Pluripotent Stem Cells, Cell Stem Cell 1:39-49.

* cited by examiner

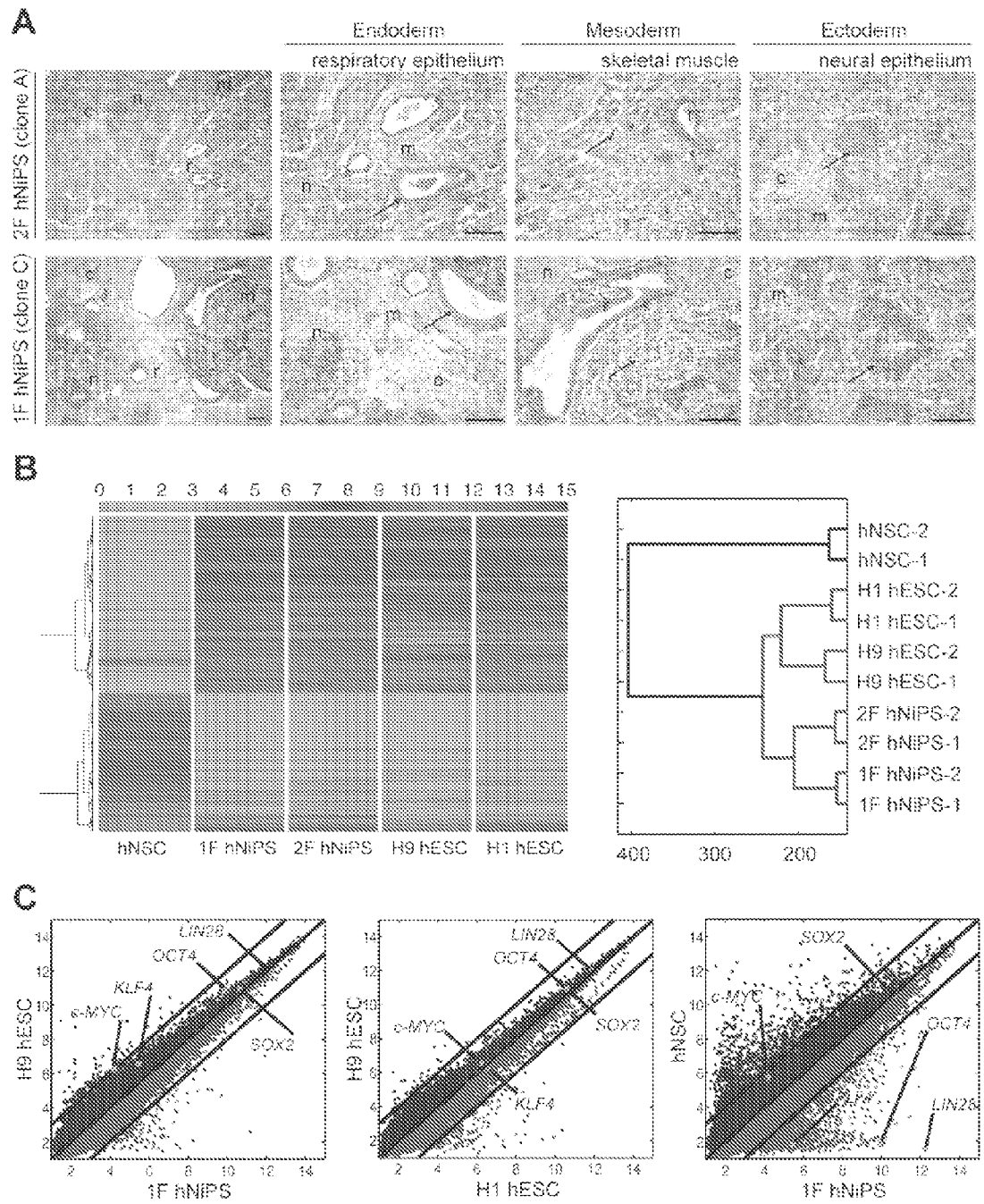

SEQUENCE LISTING

<160> NUMBER OF SEQ ID NOS: 93

<210> SEQ ID NO 1
<211> LENGTH: 1059
<212> TYPE: DNA
<213> ORGANISM: mus musculus

<400> SEQUENCE: 1

| | | | | | |
|---|---|---|---|---|---|
| atggctggac | acctggcttc | agacttcgcc | ttctcacccc | caccaggtgg | gggtgatggg | 60 |
| tcagcagggc | tggagccggg | ctgggtggat | cctcgaacct | ggctaagctt | ccaagggcct | 120 |
| ccaggtgggc | ctggaatcgg | accaggctca | gaggtattgg | ggatctcccc | atgtccgccc | 180 |
| gcatacgagt | tctgcggagg | gatggcatac | tgtggacctc | aggttggact | gggcctagtc | 240 |
| ccccaagttg | gcgtggagac | tttgcagcct | gagggccagg | caggagcacg | agtggaaagc | 300 |
| aactcagagg | gaacctcctc | tgagccctgt | gccgaccgcc | ccaatgccgt | gaagttggag | 360 |
| aaggtggaac | caactcccga | ggagtcccag | gacatgaaag | ccctgcagaa | ggagctagaa | 420 |
| cagtttgcca | agctgctgaa | gcagaagagg | atcaccttgg | ggtacaccca | ggccgacgtg | 480 |
| gggctcaccc | tgggcgttct | ctttggaaag | gtgttcagcc | agaccaccat | ctgtcgcttc | 540 |
| gaggccttgc | agctcagcct | taagaacatg | tgtaagctgc | ggcccctgct | ggagaagtgg | 600 |
| gtggaggaag | ccgacaacaa | tgagaacctt | caggagatat | gcaaatcgga | gaccctggtg | 660 |
| caggcccgga | agagaaagcg | aactagcatt | gagaaccgtg | tgaggtggag | tctggagacc | 720 |
| atgtttctga | agtgcccgaa | gccctcccta | cagcagatca | ctcacatcgc | caatcagctt | 780 |
| gggctagaga | aggatgtggt | tcgagtatgg | ttctgtaacc | ggcgccagaa | gggcaaaaga | 840 |
| tcaagtattg | agtattccca | acgagaagag | tatgaggcta | cagggacacc | tttcccaggg | 900 |
| ggggctgtat | cctttcctct | gccccaggt | ccccactttg | caccccagg | ctatggaagc | 960 |
| ccccacttca | ccacactcta | ctcagtccct | tttcctgagg | gcgaggcctt | tccctctgtt | 1020 |
| cccgtcactg | ctctgggctc | tcccatgcat | tcaaactga | | | 1059 |

<210> SEQ ID NO 2
<211> LENGTH: 352
<212> TYPE: PRT
<213> ORGANISM: mus musculus

<400> SEQUENCE: 2

Met Ala Gly His Leu Ala Ser Asp Phe Ala Phe Ser Pro Pro Pro Gly
1               5                   10                  15

Gly Gly Asp Gly Ser Ala Gly Leu Glu Pro Gly Trp Val Asp Pro Arg
            20                  25                  30

Thr Trp Leu Ser Phe Gln Gly Pro Pro Gly Gly Pro Gly Ile Gly Pro
        35                  40                  45

Gly Ser Glu Val Leu Gly Ile Ser Pro Cys Pro Pro Ala Tyr Glu Phe
    50                  55                  60

Cys Gly Gly Met Ala Tyr Cys Gly Pro Gln Val Gly Leu Gly Leu Val
65                  70                  75                  80

Pro Gln Val Gly Val Glu Thr Leu Gln Pro Gly Gln Ala Gly Ala
            85                  90                  95

Arg Val Glu Ser Asn Ser Glu Gly Thr Ser Ser Glu Pro Cys Ala Asp
            100                 105                 110

Arg Pro Asn Ala Val Lys Leu Glu Lys Val Glu Pro Thr Pro Glu Glu
            115                 120                 125

Ser Gln Asp Met Lys Ala Leu Gln Lys Glu Leu Glu Gln Phe Ala Lys

```
                      130              135               140
Leu Leu Lys Gln Lys Arg Ile Thr Leu Gly Tyr Thr Gln Ala Asp Val
145                 150                 155                 160

Gly Leu Thr Leu Gly Val Leu Phe Gly Lys Val Phe Ser Gln Thr Thr
                165                 170                 175

Ile Cys Arg Phe Glu Ala Leu Gln Leu Ser Leu Lys Asn Met Cys Lys
            180                 185                 190

Leu Arg Pro Leu Leu Glu Lys Trp Val Glu Glu Ala Asp Asn Asn Glu
                195                 200                 205

Asn Leu Gln Glu Ile Cys Lys Ser Glu Thr Leu Val Gln Ala Arg Lys
            210                 215                 220

Arg Lys Arg Thr Ser Ile Glu Asn Arg Val Arg Trp Ser Leu Glu Thr
225                 230                 235                 240

Met Phe Leu Lys Cys Pro Lys Pro Ser Leu Gln Gln Ile Thr His Ile
                245                 250                 255

Ala Asn Gln Leu Gly Leu Glu Lys Asp Val Val Arg Val Trp Phe Cys
            260                 265                 270

Asn Arg Arg Gln Lys Gly Lys Arg Ser Ser Ile Glu Tyr Ser Gln Arg
275                 280                 285

Glu Glu Tyr Glu Ala Thr Gly Thr Pro Phe Pro Gly Gly Ala Val Ser
    290                 295                 300

Phe Pro Leu Pro Pro Gly Pro His Phe Gly Thr Pro Gly Tyr Gly Ser
305                 310                 315                 320

Pro His Phe Thr Thr Leu Tyr Ser Val Pro Phe Pro Glu Gly Glu Ala
                325                 330                 335

Phe Pro Ser Val Pro Val Thr Ala Leu Gly Ser Pro Met His Ser Asn
                340                 345                 350

<210> SEQ ID NO 3
<211> LENGTH: 1083
<212> TYPE: DNA
<213> ORGANISM: homo sapiens

<400> SEQUENCE: 3
atggcgggac acctggcttc ggatttcgcc ttctcgcccc ctccaggtgg tggaggtgat    60
gggccagggg ggccggagcc gggctgggtt gatcctcgga cctggctaag cttccaaggc   120
cctcctggag ggcaggaat cgggccgggg gttgggccag ctctgaggt gtggggatt    180 cccccatgcc ccccgccgta tgagttctgt gggggatgg cgtactgtgg ccccaggtt    240 ggagtggggc tagtgcccca aggcggcttg agacctctc agcctgaggg cgaagcagga   300
gtcggggtgg agagcaactc cgatggggcc tccccggagc cctgcaccgt caccctggt   360 gccgtgaagc tggagaagga aagctggag caaaacccgg aggagtccca ggacatcaaa   420
gctctgcaga agaactcga gcaatttgcc aagctcctga gcagaagag gatcaccctg   480 ggatatacac aggccgatgt ggggctcacc ctgggggttc tatttgggaa ggtattcagc   540
caaacgacca tctgccgctt tgaggctctg cagcttagct tcaagaacat gtgtaagctg   600
cggcccttgc tgcagaagtg ggtggaggaa gctgacaaca atgaaaatct tcaggagata   660
tgcaaagcag aaaccctcgt gcaggcccga aagagaaagc gaaccagtat cgagaaccga   720
gtgagaggca acctggagaa tttgttcctg cagtgcccga acccacact gcagcagatc   780 agccacatcg cccagcagct tgggctcgag aaggatgtgg tccgagtgtg gttctgtaac   840
cggcgccaga agggcaagcg atcaagcagc gactatgcac aacgagagga ttttgaggct   900
```

```
gctgggtctc ctttctcagg gggaccagtg tcctttcctc tggccccagg gccccatttt    960
ggtaccccag gctatgggag ccctcacttc actgcactgt actcctcggt cccttccct   1020 gagggggaag ccttccccc tgtctccgtc accactctgg gctctcccat gcattcaaac   1080
tga                                                                 1083
```

<210> SEQ ID NO 4
<211> LENGTH: 360
<212> TYPE: PRT
<213> ORGANISM: homo sapiens

<400> SEQUENCE: 4

```
Met Ala Gly His Leu Ala Ser Asp Phe Ala Phe Ser Pro Pro Gly
1               5                  10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
            35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
            115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
            195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335
```

```
Val Pro Phe Pro Glu Gly Glu Ala Phe Pro Val Ser Val Thr Thr
            340                 345                 350

Leu Gly Ser Pro Met His Ser Asn
        355                 360

<210> SEQ ID NO 5
<211> LENGTH: 960
<212> TYPE: DNA
<213> ORGANISM: mus musculus

<400> SEQUENCE: 5
atgtataaca tgatggagac ggagctgaag ccgccgggcc cgcagcaagc ttcggggggc      60
ggcggcggag gaggcaacgc cacggcggcg gcgaccggcg gcaaccagaa gaacagcccg     120
gaccgcgtca gaggcccat gaacgccttc atggtatggt cccgggggca gcggcgtaag     180
atggcccagg agaaccccaa gatgcacaac tcggagatca gcaagcgcct gggcgcggag     240
tggaaacttt tgtccgagac cgagaagcgg ccgttcatcg acgaggccaa gcggctgcgc     300
gctctgcaca tgaaggagca cccggattat aaataccggc cgcggcggaa aaccaagacg     360
ctcatgaaga aggataagta cacgcttccc ggaggcttgc tggcccccgg cgggaacagc     420
atggcgagcg gggttggggt gggcgccggc ctgggtgcgg gcgtgaacca gcgcatggac     480
agctacgcgc acatgaacgg ctggagcaac ggcagctaca gcatgatgca ggagcagctg     540 ggctaccccgc agcaccnggg cctcaacgct acggcgcgg cacagatgca accgatgcac     600
cgctacgacg tcagcgcccct gcagtacaac tccatgacca gctcgcagac ctacatgaac     660
ggctcgcccc cctacagcat gtcctactcg cagcagggca ccccggtat ggcgctgggc     720 tccatgggct ctgtggtcaa gtccgaggcc agctccagcc ccccgtggt tacctcttcc     780 tcccactcca gggcgccctg ccaggccggg gacctccggg acatgatcag catgtacctc     840
cccggcgccg aggtgccgga gcccgctgcg cccagtagac tgcacatggc ccagcactac     900
cagagcggcc cggtgcccgg cacggccatt aacggcacac tgccctgtc gcacatgtga     960

<210> SEQ ID NO 6
<211> LENGTH: 319
<212> TYPE: PRT
<213> ORGANISM: mus musculus

<400> SEQUENCE: 6

Met Tyr Asn Met Met Glu Thr Glu Leu Lys Pro Pro Gly Pro Gln Gln
 1               5                  10                  15

Ala Ser Gly Gly Gly Gly Gly Gly Asn Ala Thr Ala Ala Thr
            20                  25                  30

Gly Gly Asn Gln Lys Asn Ser Pro Asp Arg Val Lys Arg Pro Met Asn
            35                  40                  45

Ala Phe Met Val Trp Ser Arg Gly Gln Arg Arg Lys Met Ala Gln Glu
     50                  55                  60

Asn Pro Lys Met His Asn Ser Glu Ile Ser Lys Arg Leu Gly Ala Glu
 65                  70                  75                  80

Trp Lys Leu Leu Ser Glu Thr Glu Lys Arg Pro Phe Ile Asp Glu Ala
                 85                  90                  95

Lys Arg Leu Arg Ala Leu His Met Lys Glu His Pro Asp Tyr Lys Tyr
            100                 105                 110

Arg Pro Arg Arg Lys Thr Lys Thr Leu Met Lys Lys Asp Lys Tyr Thr
        115                 120                 125

Leu Pro Gly Gly Leu Leu Ala Pro Gly Gly Asn Ser Met Ala Ser Gly
```

```
                      130                 135                 140
Val Gly Val Gly Ala Gly Leu Gly Ala Gly Val Asn Gln Arg Met Asp
145                 150                 155                 160

Ser Tyr Ala His Met Asn Gly Trp Ser Asn Gly Ser Tyr Ser Met Met
                165                 170                 175

Gln Glu Gln Leu Gly Tyr Pro Gln His Pro Gly Leu Asn Ala His Gly
            180                 185                 190

Ala Ala Gln Met Gln Pro Met His Arg Tyr Asp Val Ser Ala Leu Gln
        195                 200                 205

Tyr Asn Ser Met Thr Ser Ser Gln Thr Tyr Met Asn Gly Ser Pro Thr
    210                 215                 220

Tyr Ser Met Ser Tyr Ser Gln Gln Gly Thr Pro Gly Met Ala Leu Gly
225                 230                 235                 240

Ser Met Gly Ser Val Val Lys Ser Glu Ala Ser Ser Ser Pro Pro Val
                245                 250                 255

Val Thr Ser Ser His Ser Arg Ala Pro Cys Gln Ala Gly Asp Leu
            260                 265                 270

Arg Asp Met Ile Ser Met Tyr Leu Pro Gly Ala Glu Val Pro Glu Pro
        275                 280                 285

Ala Ala Pro Ser Arg Leu His Met Ala Gln His Tyr Gln Ser Gly Pro
    290                 295                 300

Val Pro Gly Thr Ala Ile Asn Gly Thr Leu Pro Leu Ser His Met
305                 310                 315

<210> SEQ ID NO 7
<211> LENGTH: 954
<212> TYPE: DNA
<213> ORGANISM: homo sapiens

<400> SEQUENCE: 7
atgtacaaca tgatggagac ggagctgaag ccgccgggcc cgcagcaaac ttcgggggc      60 ggcggcggca actccaccgc ggcggcggcc ggcggcaacc agaaaaacag cccggaccgc    120
gtcaagcggc ccatgaatgc cttcatggtg tggtcccgcg gcagcggcg caagatggcc     180 caggagaacc ccaagatgca caactcggag atcagcaagc gcctgggcgc cgagtggaaa    240
cttttgtcgg agacggagaa gcggccgttc atcgacgagg ctaagcggct gcgagcgctg    300
cacatgaagg agcaccccga ttataaatac cggcccggc ggaaaaccaa gacgctcatg     360
aagaaggata gtacacgct gcccggcggg ctgctggccc ccggcggcaa tagcatggcg     420
agcggggtcg gggtgggcgc cggcctgggc gcggcgtga accagcgcat ggacagttac     480
gcgcacatga acggctggag caacggcagc tacagcatga tgcaggacca gctgggctac    540
ccgcagcacc cgggcctcaa tgcgcacggc gcagcgcaga tgcagcccat gcaccgctac    600
gacgtgagcg ccctgcagta caactccatg accagctcgc agacctacat gaacggctcg    660
cccacctaca gcatgtccta ctcgcagcag ggcaccctg gcatggctct ggctccatg     720 ggttcggtgg tcaagtccga ggccagctcc agccccctg tggttacctc ttcctcccac    780
tccagggcgc cctgccaggc cggggacctc cgggacatga tcagcatgta tctccccggc    840
gccgaggtgc cggaacccgc cgcccccagc agacttcaca tgtcccagca ctaccagagc    900
ggcccggtgc cggcacggc cattaacggc acactgcccc tctcacacat gtga           954

<210> SEQ ID NO 8
<211> LENGTH: 317
<212> TYPE: PRT
```

<213> ORGANISM: homo sapiens

<400> SEQUENCE: 8

```
Met Tyr Asn Met Met Glu Thr Glu Leu Lys Pro Pro Gly Pro Gln Gln
1               5                   10                  15
Thr Ser Gly Gly Gly Gly Asn Ser Thr Ala Ala Ala Ala Gly Gly
            20                  25                  30
Asn Gln Lys Asn Ser Pro Asp Arg Val Lys Arg Pro Met Asn Ala Phe
        35                  40                  45
Met Val Trp Ser Arg Gly Gln Arg Arg Lys Met Ala Gln Glu Asn Pro
50                  55                  60
Lys Met His Asn Ser Glu Ile Ser Lys Arg Leu Gly Ala Glu Trp Lys
65                  70                  75                  80
Leu Leu Ser Glu Thr Glu Lys Arg Pro Phe Ile Asp Glu Ala Lys Arg
                85                  90                  95
Leu Arg Ala Leu His Met Lys Glu His Pro Asp Tyr Lys Tyr Arg Pro
            100                 105                 110
Arg Arg Lys Thr Lys Thr Leu Met Lys Lys Asp Lys Tyr Thr Leu Pro
        115                 120                 125
Gly Gly Leu Leu Ala Pro Gly Gly Asn Ser Met Ala Ser Gly Val Gly
130                 135                 140
Val Gly Ala Gly Leu Gly Ala Gly Val Asn Gln Arg Met Asp Ser Tyr
145                 150                 155                 160
Ala His Met Asn Gly Trp Ser Asn Gly Ser Tyr Ser Met Met Gln Asp
                165                 170                 175
Gln Leu Gly Tyr Pro Gln His Pro Gly Leu Asn Ala His Gly Ala Ala
            180                 185                 190
Gln Met Gln Pro Met His Arg Tyr Asp Val Ser Ala Leu Gln Tyr Asn
        195                 200                 205
Ser Met Thr Ser Ser Gln Thr Tyr Met Asn Gly Ser Pro Thr Tyr Ser
210                 215                 220
Met Ser Tyr Ser Gln Gln Gly Thr Pro Gly Met Ala Leu Gly Ser Met
225                 230                 235                 240
Gly Ser Val Val Lys Ser Glu Ala Ser Ser Pro Pro Val Val Thr
                245                 250                 255
Ser Ser Ser His Ser Arg Ala Pro Cys Gln Ala Gly Asp Leu Arg Asp
            260                 265                 270
Met Ile Ser Met Tyr Leu Pro Gly Ala Glu Val Pro Glu Pro Ala Ala
        275                 280                 285
Pro Ser Arg Leu His Met Ser Gln His Tyr Gln Ser Gly Pro Val Pro
290                 295                 300
Gly Thr Ala Ile Asn Gly Thr Leu Pro Leu Ser His Met
305                 310                 315
```

<210> SEQ ID NO 9
<211> LENGTH: 1320
<212> TYPE: DNA
<213> ORGANISM: mus musculus

<400> SEQUENCE: 9

```
atgcccctca acgtgaactt caccaacagg aactatgacc tcgactacga ctccgtacag     60
ccctatttca tctgcgacga ggaagagaat ttctatcacc agcaacagca gagcgagctg    120
cagccgcccg cgcccagtga ggatatctgg aagaaattcg agctgcttcc cacccccgcc    180
ctgtccccga gccgccgctc cgggctctgc tctccatcct atgttgcggt cgctacgtcc    240
```

```
ttctccccaa gggaagacga tgacggcggc ggtggcaact ctccaccgc cgatcagctg     300
gagatgatga ccgagttact tggaggagac atggtgaacc agagcttcat ctgcgatcct    360
gacgacgaga ccttcatcaa gaacatcatc atccaggact gtatgtggag cggtttctca    420
gccgctgcca agctggtctc ggagaagctg gcctcctacc aggctgcgcg caaagacagc    480
accagcctga gccccgcccg cgggcacagc gtctgctcca cctccagcct gtacctgcag    540
gacctcaccg ccgccgcgtc cgagtgcatt gacccctcag tggtcttttcc ctacccgctc   600
aacgacagca gctcgcccaa atcctgtacc tcgtccgatt ccacggcctt ctctccttcc    660
tcggactcgc tgctgtcctc cgagtcctcc ccacgggcca gccctgagcc cctagtgctg    720
catgaggaga caccgcccac caccagcagc gactctgaag aagagcaaga agatgaggaa    780
gaaattgatg tggtgtctgt ggagaagagg caaacccctg ccaagaggtc ggagtcgggc    840
tcatctccat cccgaggcca agcaaacct ccgcacagcc cactggtcct caagaggtgc     900
cacgtctcca ctcaccagca caactacgcc gcacccccct ccacaaggaa ggactatcca    960
gctgccaaga gggccaagtt ggacagtggc agggtcctga agcagatcag caacaaccgc   1020
aagtgctcca gccccaggtc ctcagacacg gaggaaaacg acaagaggcg acacacaac    1080
gtcttggaac gtcagaggag gaacgagctg aagcgcagct ttttgccct gcgtgaccag    1140
atccctgaat ggaaaacaa cgaaaaggcc cccaaggtag tgatcctcaa aaagccacc    1200
gcctacatcc tgtccattca agcagacgag cacaagctca cctctgaaaa ggacttattg   1260
aggaaacgac gagaacagtt gaaacacaaa ctcgaacagc ttcgaaactc tggtgcataa   1320
```

<210> SEQ ID NO 10
<211> LENGTH: 454
<212> TYPE: PRT
<213> ORGANISM: mus musculus

<400> SEQUENCE: 10

```
Leu Asp Phe Leu Trp Ala Leu Glu Thr Pro Gln Thr Ala Thr Thr Met
1               5                  10                  15

Pro Leu Asn Val Asn Phe Thr Asn Arg Asn Tyr Asp Leu Asp Tyr Asp
                20                  25                  30

Ser Val Gln Pro Tyr Phe Ile Cys Asp Glu Glu Asn Phe Tyr His
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Ala Thr Ser Phe
                85                  90                  95

Ser Pro Arg Glu Asp Asp Asp Gly Gly Gly Gly Asn Phe Ser Thr Ala
            100                 105                 110

Asp Gln Leu Glu Met Met Thr Glu Leu Leu Gly Gly Asp Met Val Asn
        115                 120                 125

Gln Ser Phe Ile Cys Asp Pro Asp Asp Glu Thr Phe Ile Lys Asn Ile
    130                 135                 140

Ile Ile Gln Asp Cys Met Trp Ser Gly Phe Ser Ala Ala Ala Lys Leu
145                 150                 155                 160

Val Ser Glu Lys Leu Ala Ser Tyr Gln Ala Ala Arg Lys Asp Ser Thr
                165                 170                 175

Ser Leu Ser Pro Ala Arg Gly His Ser Val Cys Ser Thr Ser Ser Leu
```

|     |     |     |     | 180 |     |     |     | 185 |     |     |     | 190 |     |     |
| --- | --- | --- | --- | --- | --- | --- | --- | --- | --- | --- | --- | --- | --- | --- |
| Tyr | Leu | Gln | Asp | Leu | Thr | Ala | Ala | Ser | Glu | Cys | Ile | Asp | Pro | Ser |
|     |     |     | 195 |     |     |     |     | 200 |     |     |     | 205 |     |     |
| Val | Val | Phe | Pro | Tyr | Pro | Leu | Asn | Asp | Ser | Ser | Ser | Pro | Lys | Ser | Cys |
|     |     | 210 |     |     |     |     | 215 |     |     |     |     | 220 |     |     |
| Thr | Ser | Ser | Asp | Ser | Thr | Ala | Phe | Ser | Pro | Ser | Ser | Asp | Ser | Leu | Leu |
| 225 |     |     |     |     | 230 |     |     |     |     | 235 |     |     |     |     | 240 |
| Ser | Ser | Glu | Ser | Ser | Pro | Arg | Ala | Ser | Pro | Glu | Pro | Leu | Val | Leu | His |
|     |     |     |     | 245 |     |     |     |     | 250 |     |     |     |     | 255 |     |
| Glu | Glu | Thr | Pro | Pro | Thr | Thr | Ser | Ser | Asp | Ser | Glu | Glu | Gln | Glu |
|     |     |     | 260 |     |     |     |     | 265 |     |     |     | 270 |     |     |
| Asp | Glu | Glu | Glu | Ile | Asp | Val | Val | Ser | Val | Glu | Lys | Arg | Gln | Thr | Pro |
|     |     | 275 |     |     |     |     | 280 |     |     |     |     | 285 |     |     |
| Ala | Lys | Arg | Ser | Glu | Ser | Gly | Ser | Ser | Pro | Ser | Arg | Gly | His | Ser | Lys |
|     | 290 |     |     |     |     | 295 |     |     |     |     | 300 |     |     |     |
| Pro | Pro | His | Ser | Pro | Leu | Val | Leu | Lys | Arg | Cys | His | Val | Ser | Thr | His |
| 305 |     |     |     |     | 310 |     |     |     |     | 315 |     |     |     |     | 320 |
| Gln | His | Asn | Tyr | Ala | Ala | Pro | Pro | Ser | Thr | Arg | Lys | Asp | Tyr | Pro | Ala |
|     |     |     |     | 325 |     |     |     |     | 330 |     |     |     |     | 335 |     |
| Ala | Lys | Arg | Ala | Lys | Leu | Asp | Ser | Gly | Arg | Val | Leu | Lys | Gln | Ile | Ser |
|     |     |     | 340 |     |     |     |     | 345 |     |     |     |     | 350 |     |     |
| Asn | Asn | Arg | Lys | Cys | Ser | Ser | Pro | Arg | Ser | Ser | Asp | Thr | Glu | Glu | Asn |
|     |     | 355 |     |     |     |     | 360 |     |     |     |     | 365 |     |     |
| Asp | Lys | Arg | Arg | Thr | His | Asn | Val | Leu | Glu | Arg | Gln | Arg | Arg | Asn | Glu |
|     | 370 |     |     |     |     | 375 |     |     |     |     | 380 |     |     |     |
| Leu | Lys | Arg | Ser | Phe | Phe | Ala | Leu | Arg | Asp | Gln | Ile | Pro | Glu | Leu | Glu |
| 385 |     |     |     |     | 390 |     |     |     |     | 395 |     |     |     |     | 400 |
| Asn | Asn | Glu | Lys | Ala | Pro | Lys | Val | Val | Ile | Leu | Lys | Lys | Ala | Thr | Ala |
|     |     |     |     | 405 |     |     |     |     | 410 |     |     |     |     | 415 |     |
| Tyr | Ile | Leu | Ser | Ile | Gln | Ala | Asp | Glu | His | Lys | Leu | Thr | Ser | Glu | Lys |
|     |     |     | 420 |     |     |     |     | 425 |     |     |     |     | 430 |     |     |
| Asp | Leu | Leu | Arg | Lys | Arg | Arg | Glu | Gln | Leu | Lys | His | Lys | Leu | Glu | Gln |
|     |     |     | 435 |     |     |     |     | 440 |     |     |     |     | 445 |     |     |
| Leu | Arg | Asn | Ser | Gly | Ala |
|     | 450 |     |     |     |     |

```
<210> SEQ ID NO 11
<211> LENGTH: 1320
<212> TYPE: DNA
<213> ORGANISM: homo sapiens

<400> SEQUENCE: 11
```

| | | |
|---|---|---|
| atgcccctca acgttagctt caccaacagg aactatgacc tcgactacga ctcggtgcag | 60 |
| ccgtatttct actgcgacga ggaggagaac ttctaccagc agcagcagca gagcgagctg | 120 |
| cagcccccgg cgcccagcga ggatatctgg aagaaattcg agctgctgcc caccccgccc | 180 |
| ctgtccccta gccgccgctc cgggctctgc tcgccctcct acgttgcggt cacacccttc | 240 |
| tcccttcggg gagacaacga cggcggtggc gggagcttct ccacggccga ccagctggag | 300 |
| atggtgaccg agctgctggg aggagacatg gtgaaccaga gtttcatctg cgaccccgac | 360 |
| gacgagacct tcatcaaaaa catcatcatc caggactgta tgtggagcgg cttctcggcc | 420 |
| gccgccaagc tgtctctcaga gaagctggcc tcctaccagg ctgcgcgcaa agacagcggc | 480 |
| agcccgaacc ccgccgcgg ccacagcgtc tgctccacct ccagcttgta cctgcaggat | 540 |

```
ctgagcgccg ccgcctcaga gtgcatcgac ccctcggtgg tcttccccta ccctctcaac    600
gacagcagct cgcccaagtc ctgcgcctcg caagactcca gcgccttctc tccgtcctcg    660
gattctctgc tctcctcgac ggagtcctcc ccgcagggca gccccgagcc cctggtgctc    720
catgaggaga caccgcccac caccagcagc gactctgagg aggaacaaga agatgaggaa    780
gaaatcgatg ttgtttctgt ggaaaagagg caggctcctg gcaaaaggtc agagtctgga    840
tcaccttctg ctggaggcca cagcaaacct cctcacagcc cactggtcct caagaggtgc    900
cacgtctcca cacatcagca aactacgca gcgcctccct ccactcggaa ggactatcct    960
gctgccaaga gggtcaagtt ggacagtgtc agagtcctga cagatcag caacaaccga    1020
aaatgcacca gccccaggtc ctcggacacc gaggagaatg tcaagaggcg aacacacaac    1080
gtcttggagc gccagaggag gaacgagcta aacggagct tttttgccct gcgtgaccag    1140
atcccggagt tggaaaacaa tgaaaaggcc cccaaggtag ttatccttaa aaagccaca    1200
gcatacatcc tgtccgtcca agcagaggag caaaagctca tttctgaaga ggacttgttg    1260
cggaaacgac gagaacagtt gaaacacaaa cttgaacagc tacggaactc ttgtgcgtaa    1320
```

<210> SEQ ID NO 12
<211> LENGTH: 454
<212> TYPE: PRT
<213> ORGANISM: homo sapiens

<400> SEQUENCE: 12

Leu Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
                100                 105                 110

Gln Leu Glu Met Val Thr Glu Leu Leu Gly Gly Asp Met Val Asn Gln
            115                 120                 125

Ser Phe Ile Cys Asp Pro Asp Asp Glu Thr Phe Ile Lys Asn Ile Ile
        130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
                180                 185                 190

Leu Gln Asp Leu Ser Ala Ala Ala Ser Glu Cys Ile Asp Pro Ser Val
            195                 200                 205

Val Phe Pro Tyr Pro Leu Asn Asp Ser Ser Ser Pro Lys Ser Cys Ala
        210                 215                 220

Ser Gln Asp Ser Ser Ala Phe Ser Pro Ser Ser Asp Ser Leu Leu Ser
225                 230                 235                 240

```
Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450

<210> SEQ ID NO 13
<211> LENGTH: 1425
<212> TYPE: DNA
<213> ORGANISM: mus musculus

<400> SEQUENCE: 13
atggctgtca gcgacgctct gctcccgtcc ttctccacgt tcgcgtccgg cccggcggga      60
agggagaaga cactgcgtcc agcaggtgcc ccgactaacc gttggcgtga ggaactctct     120
cacatgaagc gacttccccc acttccggc cgcccctacg acctggcggc gacggtggcc     180
acagacctgg agagtggcgg agctggtgca gcttgcagca gtaacaaccc ggccctccta     240
gcccggaggg agaccgagga gttcaacgac ctcctggacc tagactttat ccttttccaac    300 tcgctaaccc accaggaatc ggtggccgcc accgtgacca cctcggcgtc agcttcatcc     360
tcgtcttccc cggcgagcag cggccctgcc agcgcgccct ccacctgcag cttcagctat     420
ccgatccggg ccgggggtga cccggggcgtg gctgccagaa acacaggtgg agggctcctc    480
tacagccgag aatctgcgcc acctcccacg gcccccttca acctggggga catcaatgac     540
gtgagcccct cgggcggctt cgtggctgag ctcctgcggc ggagttggac ccagtatac     600 attccgccac agcagcctca gccgccaggt gggggggctga tgggcaagtt tgtgctgaag    660
gcgtctctga ccacccctgg cagcgagtac agcagccctt cggtcatcag tgttagcaaa    720
ggaagcccag acggcagcca cccgtggta gtgcgccct acagcggtgg cccgccgcgc      780
atgtgcccca agattaagca agaggcggtc ccgtcctgca cggtcagccg gtccctagag     840
gcccatttga gcgctggacc ccagctcagc aacggccacc ggcccaacac acacgacttc     900
```

```
cccctggggc ggcagctccc caccaggact acccctacac tgagtcccga ggaactgctg    960
aacagcaggg actgtcaccc tggcctgcct cttcccccag gattccatcc ccatccgggg   1020
gccaactacc ctcctttcct gccagaccag atgcagtcac aagtcccctc tctccattat   1080
caagagctca tgccaccggg ttcctgcctg ccagaggagc ccaagccaaa gaggggaaga   1140
aggtcgtggc cccggaaaag aacagccacc cacacttgtg actatgcagg ctgtggcaaa   1200
acctatacca gagttctca tctcaaggca cacctgcgaa ctcacacagg cgagaaacct    1260
taccactgtg actgggacgg ctgtgggtgg aaattcgccc gctccgatga actgaccagg   1320
cactaccgca aacacacagg gcaccggccc tttcagtgcc agaagtgtga cagggccttt   1380
tccaggtcgg accaccttgc cttacacatg aagaggcact tttaa                   1425
```

<210> SEQ ID NO 14
<211> LENGTH: 474
<212> TYPE: PRT
<213> ORGANISM: mus musculus

<400> SEQUENCE: 14

```
Met Ala Val Ser Asp Ala Leu Leu Pro Ser Phe Ser Thr Phe Ala Ser
1               5                   10                  15

Gly Pro Ala Gly Arg Glu Lys Thr Leu Arg Pro Ala Gly Ala Pro Thr
            20                  25                  30

Asn Arg Trp Arg Glu Glu Leu Ser His Met Lys Arg Leu Pro Pro Leu
        35                  40                  45

Pro Gly Arg Pro Tyr Asp Leu Ala Ala Thr Val Ala Thr Asp Leu Glu
    50                  55                  60

Ser Gly Gly Ala Gly Ala Ala Cys Ser Ser Asn Asn Pro Ala Leu Leu
65                  70                  75                  80

Ala Arg Arg Glu Thr Glu Glu Phe Asn Asp Leu Leu Asp Leu Asp Phe
                85                  90                  95

Ile Leu Ser Asn Ser Leu Thr His Gln Glu Ser Val Ala Ala Thr Val
            100                 105                 110

Thr Thr Ser Ala Ser Ala Ser Ser Ser Ser Pro Ala Ser Ser Gly
        115                 120                 125

Pro Ala Ser Ala Pro Ser Thr Cys Ser Phe Ser Tyr Pro Ile Arg Ala
    130                 135                 140

Gly Gly Asp Pro Gly Val Ala Ala Arg Asn Thr Gly Gly Gly Leu Leu
145                 150                 155                 160

Tyr Ser Arg Glu Ser Ala Pro Pro Thr Ala Pro Phe Asn Leu Gly
                165                 170                 175

Asp Ile Asn Asp Val Ser Pro Ser Gly Gly Phe Val Ala Glu Leu Leu
            180                 185                 190

Arg Pro Glu Leu Asp Pro Val Tyr Ile Pro Pro Gln Gln Pro Gln Pro
        195                 200                 205

Pro Gly Gly Gly Leu Met Gly Lys Phe Val Leu Lys Ala Ser Leu Thr
    210                 215                 220

Thr Pro Gly Ser Glu Tyr Ser Ser Pro Ser Val Ile Ser Val Ser Lys
225                 230                 235                 240

Gly Ser Pro Asp Gly Ser His Pro Val Val Ala Pro Tyr Ser Gly
                245                 250                 255

Gly Pro Pro Arg Met Cys Pro Lys Ile Lys Gln Glu Ala Val Pro Ser
        260                 265                 270

Cys Thr Val Ser Arg Ser Leu Glu Ala His Leu Ser Ala Gly Pro Gln
```

|   |   |   | 275 |   |   |   | 280 |   |   |   | 285 |   |   |
|---|---|---|-----|---|---|---|-----|---|---|---|-----|---|---|

Leu Ser Asn Gly His Arg Pro Asn Thr His Asp Phe Pro Leu Gly Arg
    290             295             300

Gln Leu Pro Thr Arg Thr Pro Thr Leu Ser Pro Glu Glu Leu Leu
305             310             315             320

Asn Ser Arg Asp Cys His Pro Gly Leu Pro Leu Pro Pro Gly Phe His
                325             330             335

Pro His Pro Gly Ala Asn Tyr Pro Pro Phe Leu Pro Asp Gln Met Gln
            340             345             350

Ser Gln Val Pro Ser Leu His Tyr Gln Glu Leu Met Pro Pro Gly Ser
        355             360             365

Cys Leu Pro Glu Glu Pro Lys Pro Lys Arg Gly Arg Arg Ser Trp Pro
370             375             380

Arg Lys Arg Thr Ala Thr His Thr Cys Asp Tyr Ala Gly Cys Gly Lys
385             390             395             400

Thr Tyr Thr Lys Ser Ser His Leu Lys Ala His Leu Arg Thr His Thr
            405             410             415

Gly Glu Lys Pro Tyr His Cys Asp Trp Asp Gly Cys Gly Trp Lys Phe
        420             425             430

Ala Arg Ser Asp Glu Leu Thr Arg His Tyr Arg Lys His Thr Gly His
            435             440             445

Arg Pro Phe Gln Cys Gln Lys Cys Asp Arg Ala Phe Ser Arg Ser Asp
450             455             460

His Leu Ala Leu His Met Lys Arg His Phe
465             470

<210> SEQ ID NO 15
<211> LENGTH: 1413
<212> TYPE: DNA
<213> ORGANISM: homo sapiens

<400> SEQUENCE: 15
atggctgtca gcgacgcgct gctcccatct ttctccacgt tcgcgtctgg cccggcggga      60
agggagaaga cactgcgtca agcaggtgcc ccgaataacc gctggcggga ggagctctcc     120
cacatgaagc gacttccccc agtgcttccc ggccgcccct atgacctggc ggcggcgacc     180
gtggccacag acctggagag cggcggagcc ggtgcggctt cggcggtag caacctggcg      240 cccctacctc ggagagagac cgaggagttc aacgatctcc tggacctgga ctttattctc     300
tccaattcgc tgacccatcc tccggagtca gtggccgcca ccgtgtcctc gtcagcgtca     360
gcctcctctt cgtcgtcgcc gtcgagcagc ggccctgcca gcgcgccctc cacctgcagc     420
ttcacctatc cgatccgggc cgggaacgac ccgggcgtgg cgccgggcgg cacgggcgga     480
ggcctcctct atggcaggga gtccgctccc cctccgacgg ctcccttcaa cctggcggac     540
atcaacgacg tgagccctc gggcggcttc gtggccgagc cctgcggcc agaattggac      600 ccggtgtaca ttccgccgca gcagccgcag ccgccaggtg gcgggctgat gggcaagttc     660
gtgctgaagg cgtcgctgag cgcccctggc agcgagtacg gcagcccgtc ggtcatcagc     720
gtcagcaaag gcagccctga cggcagccac cggtggtgg tggcgcccta aacggcggg      780 ccgccgcgca cgtgccccaa gatcaagcag gaggcggtct cttcgtgcac ccacttgggc     840
gctggacccc ctctcagcaa tggccaccgg ccggctgcac acgacttccc cctggggcgg     900
cagtccccca gcaggactac cccgaccctg ggtcttgagg aagtgctgag cagcagggac     960
tgtcaccctg ccctgccgct tcctcccggc ttccatcccc accgggggcc caattaccca    1020

```
tccttcctgc ccgatcagat gcagccgcaa gtcccgccgc tccattacca agagctcatg    1080
ccacccggtt cctgcatgcc agaggagccc aagccaaaga ggggaagacg atcgtggccc    1140
cggaaaagga ccgccaccca cacttgtgat tacgcgggct gcggcaaaac ctacacaaag    1200
agttcccatc tcaaggcaca cctgcgaacc cacacaggtg agaaaccta ccactgtgac     1260
```

```
agttcccatc tcaaggcaca cctgcgaacc cacacaggtg agaaaccta ccactgtgac     1260 tgggacggct gtggatggaa attcgcccgc tcagatgaac tgaccaggca ctaccgtaaa    1320
cacacggggc accgcccgtt ccagtgccaa aaatgcgacc gagcattttc caggtcggac    1380
cacctcgcct acacatgaa gaggcatttt taa                                  1413
```

<210> SEQ ID NO 16
<211> LENGTH: 469
<212> TYPE: PRT
<213> ORGANISM: homo sapiens

<400> SEQUENCE: 16

```
Met Ala Val Ser Asp Ala Leu Leu Pro Ser Phe Ser Thr Phe Ala Ser
1               5                   10                  15

Gly Pro Ala Gly Arg Glu Lys Thr Leu Arg Gln Ala Gly Ala Pro Asn
            20                  25                  30

Asn Arg Trp Arg Glu Glu Leu Ser His Met Lys Arg Leu Pro Pro Val
        35                  40                  45

Leu Pro Gly Arg Pro Tyr Asp Leu Ala Ala Ala Thr Val Ala Thr Asp
    50                  55                  60

Leu Glu Ser Gly Gly Ala Gly Ala Ala Cys Gly Gly Ser Asn Leu Ala
65                  70                  75                  80

Pro Leu Pro Arg Arg Glu Thr Glu Glu Phe Asn Asp Leu Leu Asp Leu
                85                  90                  95

Asp Phe Ile Leu Ser Asn Ser Leu Thr His Pro Pro Glu Ser Val Ala
            100                 105                 110

Ala Thr Val Ser Ser Ser Ala Ser Ala Ser Ser Ser Ser Pro Ser
        115                 120                 125

Ser Ser Gly Pro Ala Ser Ala Pro Ser Thr Cys Ser Phe Thr Tyr Pro
130                 135                 140

Ile Arg Ala Gly Asn Asp Pro Gly Val Ala Pro Gly Gly Thr Gly Gly
145                 150                 155                 160

Gly Leu Leu Tyr Gly Arg Glu Ser Ala Pro Pro Thr Ala Pro Phe
                165                 170                 175

Asn Leu Ala Asp Ile Asn Asp Val Ser Pro Ser Gly Gly Phe Val Ala
            180                 185                 190

Glu Leu Leu Arg Pro Glu Leu Asp Pro Val Tyr Ile Pro Pro Gln Gln
        195                 200                 205

Pro Gln Pro Pro Gly Gly Gly Leu Met Gly Lys Phe Val Leu Lys Ala
    210                 215                 220

Ser Leu Ser Ala Pro Gly Ser Glu Tyr Gly Ser Pro Ser Val Ile Ser
225                 230                 235                 240

Val Ser Lys Gly Ser Pro Asp Gly Ser His Pro Val Val Ala Pro
                245                 250                 255

Tyr Asn Gly Gly Pro Pro Arg Thr Cys Pro Lys Ile Lys Gln Glu Ala
            260                 265                 270

Val Ser Ser Cys Thr His Leu Gly Ala Gly Pro Pro Leu Ser Asn Gly
        275                 280                 285

His Arg Pro Ala Ala His Asp Phe Pro Leu Gly Arg Gln Leu Pro Ser
    290                 295                 300
```

Arg Thr Thr Pro Thr Leu Gly Leu Glu Glu Val Leu Ser Ser Arg Asp
305                 310                 315                 320

Cys His Pro Ala Leu Pro Leu Pro Pro Gly Phe His Pro His Pro Gly
                325                 330                 335

Pro Asn Tyr Pro Ser Phe Leu Pro Asp Gln Met Gln Pro Gln Val Pro
            340                 345                 350

Pro Leu His Tyr Gln Glu Leu Met Pro Pro Gly Ser Cys Met Pro Glu
        355                 360                 365

Glu Pro Lys Pro Lys Arg Gly Arg Arg Ser Trp Pro Arg Lys Arg Thr
    370                 375                 380

Ala Thr His Thr Cys Asp Tyr Ala Gly Cys Gly Lys Thr Tyr Thr Lys
385                 390                 395                 400

Ser Ser His Leu Lys Ala His Leu Arg Thr His Thr Gly Glu Lys Pro
                405                 410                 415

Tyr His Cys Asp Trp Asp Gly Cys Gly Trp Lys Phe Ala Arg Ser Asp
            420                 425                 430

Glu Leu Thr Arg His Tyr Arg Lys His Thr Gly His Arg Pro Phe Gln
        435                 440                 445

Cys Gln Lys Cys Asp Arg Ala Phe Ser Arg Ser Asp His Leu Ala Leu
    450                 455                 460

His Met Lys Arg His
465

<210> SEQ ID NO 17
<211> LENGTH: 23
<212> TYPE: DNA
<213> ORGANISM: artificial sequence
<220> FEATURE:
<223> OTHER INFORMATION: /note="Description of artificial sequence:
      pMXs-Oct4 PF"

<400> SEQUENCE: 17
tggtacggga aatcacaagt ttg                                         23

<210> SEQ ID NO 18
<211> LENGTH: 26
<212> TYPE: DNA
<213> ORGANISM: artificial sequence
<220> FEATURE:
<223> OTHER INFORMATION: /note="Description of artificial sequence:
      pMXs-Oct4 PR"

<400> SEQUENCE: 18
gtcatagttc ctgttggtga agttca                                      26

<210> SEQ ID NO 19
<211> LENGTH: 17
<212> TYPE: DNA
<213> ORGANISM: artificial sequence
<220> FEATURE:
<223> OTHER INFORMATION: /note="Description of artificial sequence:
      pMXs-Oct4 Probe (6FAM attached 5', MGB attached 3')"

<400> SEQUENCE: 19
cttcaccatg cccctca                                                17

<210> SEQ ID NO 20
<211> LENGTH: 22
<212> TYPE: DNA
<213> ORGANISM: artificial sequence
<220> FEATURE:

```
<223> OTHER INFORMATION: /note="Description of artificial sequence:
      pMXs-Sox2 PF"

<400> SEQUENCE: 20
gtgtggtggt acgggaaatc ac                                              22

<210> SEQ ID NO 21
<211> LENGTH: 21
<212> TYPE: DNA
<213> ORGANISM: artificial sequence
<220> FEATURE:
<223> OTHER INFORMATION: /note="Description of artificial sequence:
      pMXs-Sox2 PR"

<400> SEQUENCE: 21
ttcagctccg tctccatcat g                                               21

<210> SEQ ID NO 22
<211> LENGTH: 21
<212> TYPE: DNA
<213> ORGANISM: artificial sequence
<220> FEATURE:
<223> OTHER INFORMATION: /note="Description of artificial sequence:
      pMXs-Sox2 Probe (6FAM attached 5', MGB attached 3')"

<400> SEQUENCE: 22
tgtacaaaaa agcaggcttg t                                               21

<210> SEQ ID NO 23
<211> LENGTH: 21
<212> TYPE: DNA
<213> ORGANISM: artificial sequence
<220> FEATURE:
<223> OTHER INFORMATION: /note="Description of artificial sequence:
      pMXs-Klf4 PF"

<400> SEQUENCE: 23
gtgtggtggt acgggaaatc a                                               21

<210> SEQ ID NO 24
<211> LENGTH: 18
<212> TYPE: DNA
<213> ORGANISM: artificial sequence
<220> FEATURE:
<223> OTHER INFORMATION: /note="Description of artificial sequence:
      pMXs-Klf4 PR"

<400> SEQUENCE: 24
cgcgaacgtg gagaagga                                                   18

<210> SEQ ID NO 25
<211> LENGTH: 18
<212> TYPE: DNA
<213> ORGANISM: artificial sequence
<220> FEATURE:
<223> OTHER INFORMATION: /note="Description of artificial sequence:
      pMXs-Klf4 Probe (6FAM attached 5', MGB attached 3')"

<400> SEQUENCE: 25
cttcaccatg gctgtcag                                                   18

<210> SEQ ID NO 26
<211> LENGTH: 23
<212> TYPE: DNA
<213> ORGANISM: artificial sequence
<220> FEATURE:
<223> OTHER INFORMATION: /note="Description of artificial sequence:
```

-continued pMXs-cMyc PF"

<400> SEQUENCE: 26
tggtacggga aatcacaagt ttg                                    23

<210> SEQ ID NO 27
<211> LENGTH: 26
<212> TYPE: DNA
<213> ORGANISM: artificial sequence
<220> FEATURE:
<223> OTHER INFORMATION: /note="Description of artificial sequence:
    pMXs-cMyc PR"

<400> SEQUENCE: 27
gtcatagttc ctgttggtga agttca                                 26

<210> SEQ ID NO 28
<211> LENGTH: 17
<212> TYPE: DNA
<213> ORGANISM: artificial sequence
<220> FEATURE:
<223> OTHER INFORMATION: /note="Description of artificial sequence:
    pMXs-cMyc Probe (6FAM attached 5', MGB attached 3')"

<400> SEQUENCE: 28
cttcaccatg cccctca                                           17

<210> SEQ ID NO 29
<211> LENGTH: 25
<212> TYPE: DNA
<213> ORGANISM: artificial sequence
<220> FEATURE:
<223> OTHER INFORMATION: /note="Description of artificial sequence:
    Nanog PF"

<400> SEQUENCE: 29
aaccagtggt tgaatactag caatg                                  25

<210> SEQ ID NO 30
<211> LENGTH: 22
<212> TYPE: DNA
<213> ORGANISM: artificial sequence
<220> FEATURE:
<223> OTHER INFORMATION: /note="Description of artificial sequence:
    Nanog PR"

<400> SEQUENCE: 30
ctgcaatgga tgctgggata ct                                     22

<210> SEQ ID NO 31
<211> LENGTH: 17
<212> TYPE: DNA
<213> ORGANISM: artificial sequence
<220> FEATURE:
<223> OTHER INFORMATION: /note="Description of artificial sequence:
    Nanog Probe (6FAM attached 5', MGB attached 3')"

<400> SEQUENCE: 31
tcagaagggc tcagcac                                           17

<210> SEQ ID NO 32
<211> LENGTH: 23
<212> TYPE: DNA
<213> ORGANISM: artificial sequence
<220> FEATURE:
<223> OTHER INFORMATION: /note="Description of artificial sequence:
    ACTB PF"

```
<400> SEQUENCE: 32
tcaagatcat tgctcctcct gag                                           23

<210> SEQ ID NO 33
<211> LENGTH: 21
<212> TYPE: DNA
<213> ORGANISM: artificial sequence
<220> FEATURE:
<223> OTHER INFORMATION: /note="Description of artificial sequence:
      ACTB PR"

<400> SEQUENCE: 33
acatctgctg gaaggtggac a                                             21

<210> SEQ ID NO 34
<211> LENGTH: 20
<212> TYPE: DNA
<213> ORGANISM: artificial sequence
<220> FEATURE:
<223> OTHER INFORMATION: /note="Description of artificial sequence:
      AFP PF"

<400> SEQUENCE: 34
agcagcttgg tggtggatga                                               20

<210> SEQ ID NO 35
<211> LENGTH: 21
<212> TYPE: DNA
<213> ORGANISM: artificial sequence
<220> FEATURE:
<223> OTHER INFORMATION: /note="Description of artificial sequence:
      AFP PR"

<400> SEQUENCE: 35
cctgagcttg gcacagatcc t                                             21

<210> SEQ ID NO 36
<211> LENGTH: 21
<212> TYPE: DNA
<213> ORGANISM: artificial sequence
<220> FEATURE:
<223> OTHER INFORMATION: /note="Description of artificial sequence:
      CDH1 (E-CAD) PF"

<400> SEQUENCE: 36
ttgaggccaa gcagcagtac a                                             21

<210> SEQ ID NO 37
<211> LENGTH: 20
<212> TYPE: DNA
<213> ORGANISM: artificial sequence
<220> FEATURE:
<223> OTHER INFORMATION: /note="Description of artificial sequence:
      CDH1 (E-CAD) PR"

<400> SEQUENCE: 37
atccagcaca tccacggtga                                               20

<210> SEQ ID NO 38
<211> LENGTH: 25
<212> TYPE: DNA
<213> ORGANISM: artificial sequence
<220> FEATURE:
<223> OTHER INFORMATION: /note="Description of artificial sequence:
      CDX2 PF"
```

```
<400> SEQUENCE: 38
tcactacagt cgctacatca ccatc                                              25

<210> SEQ ID NO 39
<211> LENGTH: 22
<212> TYPE: DNA
<213> ORGANISM: artificial sequence
<220> FEATURE:
<223> OTHER INFORMATION: /note="Description of artificial sequence:
      CDX2 PR"

<400> SEQUENCE: 39
ttaacctgcc tctcagagag cc                                                 22

<210> SEQ ID NO 40
<211> LENGTH: 20
<212> TYPE: DNA
<213> ORGANISM: artificial sequence
<220> FEATURE:
<223> OTHER INFORMATION: /note="Description of artificial sequence:
      DNMT3B PF"

<400> SEQUENCE: 40
gctcacaggg cccgatactt                                                    20

<210> SEQ ID NO 41
<211> LENGTH: 22
<212> TYPE: DNA
<213> ORGANISM: artificial sequence
<220> FEATURE:
<223> OTHER INFORMATION: /note="Description of artificial sequence:
      DNMT3B PR"

<400> SEQUENCE: 41
gcagtcctgc agctcgagtt ta                                                 22

<210> SEQ ID NO 42
<211> LENGTH: 20
<212> TYPE: DNA
<213> ORGANISM: artificial sequence
<220> FEATURE:
<223> OTHER INFORMATION: /note="Description of artificial sequence:
      DPPA4 PF"

<400> SEQUENCE: 42
tggtgtcagg tggtgtgtgg                                                    20

<210> SEQ ID NO 43
<211> LENGTH: 20
<212> TYPE: DNA
<213> ORGANISM: artificial sequence
<220> FEATURE:
<223> OTHER INFORMATION: /note="Description of artificial sequence:
      DPPA4 PR"

<400> SEQUENCE: 43
ccaggcttga ccagcatgaa                                                    20

<210> SEQ ID NO 44
<211> LENGTH: 21
<212> TYPE: DNA
<213> ORGANISM: artificial sequence
<220> FEATURE:
<223> OTHER INFORMATION: /note="Description of artificial sequence:
      FGF2 PF"

<400> SEQUENCE: 44
```

```
ggcaagatgc aggagagagg a                                              21

<210> SEQ ID NO 45
<211> LENGTH: 20
<212> TYPE: DNA
<213> ORGANISM: artificial sequence
<220> FEATURE:
<223> OTHER INFORMATION: /note="Description of artificial sequence:
      FGF2 PR"

<400> SEQUENCE: 45
gccacgtgag agcagagcat                                                20

<210> SEQ ID NO 46
<211> LENGTH: 20
<212> TYPE: DNA
<213> ORGANISM: artificial sequence
<220> FEATURE:
<223> OTHER INFORMATION: /note="Description of artificial sequence:
      FOXF1 PF"

<400> SEQUENCE: 46
aaaggagcca cgaagcaagc                                                20

<210> SEQ ID NO 47
<211> LENGTH: 21
<212> TYPE: DNA
<213> ORGANISM: artificial sequence
<220> FEATURE:
<223> OTHER INFORMATION: /note="Description of artificial sequence:
      FOXF1 PR"

<400> SEQUENCE: 47
aggctgaagc gaaggaagag g                                              21

<210> SEQ ID NO 48
<211> LENGTH: 25
<212> TYPE: DNA
<213> ORGANISM: artificial sequence
<220> FEATURE:
<223> OTHER INFORMATION: /note="Description of artificial sequence:
      GAPDH PF"

<400> SEQUENCE: 48
ctggtaaagt ggatattgtt gccat                                          25

<210> SEQ ID NO 49
<211> LENGTH: 26
<212> TYPE: DNA
<213> ORGANISM: artificial sequence
<220> FEATURE:
<223> OTHER INFORMATION: /note="Description of artificial sequence:
      GAPDH PR"

<400> SEQUENCE: 49
tggaatcata ttggaacatg taaacc                                         26

<210> SEQ ID NO 50
<211> LENGTH: 22
<212> TYPE: DNA
<213> ORGANISM: artificial sequence
<220> FEATURE:
<223> OTHER INFORMATION: /note="Description of artificial sequence:
      GATA6 PF"

<400> SEQUENCE: 50
```
tgtgcgttca tggagaagat ca                                           22

<210> SEQ ID NO 51
<211> LENGTH: 27
<212> TYPE: DNA
<213> ORGANISM: artificial sequence
<220> FEATURE:
<223> OTHER INFORMATION: /note="Description of artificial sequence:
     GATA6 PR"

<400> SEQUENCE: 51
tttgataaga gacctcatga accgact                                      27

<210> SEQ ID NO 52
<211> LENGTH: 21
<212> TYPE: DNA
<213> ORGANISM: artificial sequence
<220> FEATURE:
<223> OTHER INFORMATION: /note="Description of artificial sequence:
     GDF3 PF"

<400> SEQUENCE: 52
ttggcacaag tggatcattg c                                            21

<210> SEQ ID NO 53
<211> LENGTH: 21
<212> TYPE: DNA
<213> ORGANISM: artificial sequence
<220> FEATURE:
<223> OTHER INFORMATION: /note="Description of artificial sequence:
     GDF3 PR"

<400> SEQUENCE: 53
ttggcacaag tggatcattg c                                            21

<210> SEQ ID NO 54
<211> LENGTH: 20
<212> TYPE: DNA
<213> ORGANISM: artificial sequence
<220> FEATURE:
<223> OTHER INFORMATION: /note="Description of artificial sequence:
     HAND1 PF"

<400> SEQUENCE: 54
tcccttttcc gcttgctctc                                              20

<210> SEQ ID NO 55
<211> LENGTH: 20
<212> TYPE: DNA
<213> ORGANISM: artificial sequence
<220> FEATURE:
<223> OTHER INFORMATION: /note="Description of artificial sequence:
     HAND1 PR"

<400> SEQUENCE: 55
catcgcctac ctgatggacg                                              20

<210> SEQ ID NO 56
<211> LENGTH: 26
<212> TYPE: DNA
<213> ORGANISM: artificial sequence
<220> FEATURE:
<223> OTHER INFORMATION: /note="Description of artificial sequence:
     KLF4 endo PF"

<400> SEQUENCE: 56
acagtctgtt atgcactgtg gtttca                                       26

<210> SEQ ID NO 57
<211> LENGTH: 27
<212> TYPE: DNA
<213> ORGANISM: artificial sequence
<220> FEATURE:
<223> OTHER INFORMATION: /note="Description of artificial sequence:
    KLF4 endo PR"

<400> SEQUENCE: 57
catttgttct gcttaaggca tacttgg                                       27

<210> SEQ ID NO 58
<211> LENGTH: 20
<212> TYPE: DNA
<213> ORGANISM: artificial sequence
<220> FEATURE:
<223> OTHER INFORMATION: /note="Description of artificial sequence:
    KLF4 viral PF"

<400> SEQUENCE: 58
gtcggaccac ctcgccttac                                               20

<210> SEQ ID NO 59
<211> LENGTH: 22
<212> TYPE: DNA
<213> ORGANISM: artificial sequence
<220> FEATURE:
<223> OTHER INFORMATION: /note="Description of artificial sequence:
    KLF4 viral PR"

<400> SEQUENCE: 59
tttatcgtcg accactgtgc tg                                            22

<210> SEQ ID NO 60
<211> LENGTH: 23
<212> TYPE: DNA
<213> ORGANISM: artificial sequence
<220> FEATURE:
<223> OTHER INFORMATION: /note="Description of artificial sequence:
    LIN28 PF"

<400> SEQUENCE: 60
ggaggccaag aaagggaata tga                                           23

<210> SEQ ID NO 61
<211> LENGTH: 24
<212> TYPE: DNA
<213> ORGANISM: artificial sequence
<220> FEATURE:
<223> OTHER INFORMATION: /note="Description of artificial sequence:
    LIN28 PR"

<400> SEQUENCE: 61
aacaatcttg tggccacttt gaca                                          24

<210> SEQ ID NO 62
<211> LENGTH: 19
<212> TYPE: DNA
<213> ORGANISM: artificial sequence
<220> FEATURE:
<223> OTHER INFORMATION: /note="Description of artificial sequence:
    MYC PF"

<400> SEQUENCE: 62
ccagcagcga ctctgagga                                                19

<210> SEQ ID NO 63
<211> LENGTH: 21
<212> TYPE: DNA
<213> ORGANISM: artificial sequence
<220> FEATURE:
<223> OTHER INFORMATION: /note="Description of artificial sequence:
      MYC PR"

<400> SEQUENCE: 63
gagcctgcct cttttccaca g                                              21

<210> SEQ ID NO 64
<211> LENGTH: 19
<212> TYPE: DNA
<213> ORGANISM: artificial sequence
<220> FEATURE:
<223> OTHER INFORMATION: /note="Description of artificial sequence:
      NANOG PF"

<400> SEQUENCE: 64
cctgtgattt gtgggcctg                                                 19

<210> SEQ ID NO 65
<211> LENGTH: 21
<212> TYPE: DNA
<213> ORGANISM: artificial sequence
<220> FEATURE:
<223> OTHER INFORMATION: /note="Description of artificial sequence:
      NANOG PR"

<400> SEQUENCE: 65
gacagtctcc gtgtgaggca t                                              21

<210> SEQ ID NO 66
<211> LENGTH: 20
<212> TYPE: DNA
<213> ORGANISM: artificial sequence
<220> FEATURE:
<223> OTHER INFORMATION: /note="Description of artificial sequence:
      NCAM1 PF"

<400> SEQUENCE: 66
tcatgtgcat tgcggtcaac                                                20

<210> SEQ ID NO 67
<211> LENGTH: 20
<212> TYPE: DNA
<213> ORGANISM: artificial sequence
<220> FEATURE:
<223> OTHER INFORMATION: /note="Description of artificial sequence:
      NCAM1 PR"

<400> SEQUENCE: 67
acgatgggct ccttggactc                                                20

<210> SEQ ID NO 68
<211> LENGTH: 22
<212> TYPE: DNA
<213> ORGANISM: artificial sequence
<220> FEATURE:
<223> OTHER INFORMATION: /note="Description of artificial sequence:
      OCT4 endo PF"

<400> SEQUENCE: 68
ggaggaattg ggaacacaaa gg                                             22

```
<210> SEQ ID NO 69
<211> LENGTH: 22
<212> TYPE: DNA
<213> ORGANISM: artificial sequence
<220> FEATURE:
<223> OTHER INFORMATION: /note="Description of artificial sequence:
      OCT4 endo PR"

<400> SEQUENCE: 69
aacttcacct tccctccaac ca                                              22

<210> SEQ ID NO 70
<211> LENGTH: 21
<212> TYPE: DNA
<213> ORGANISM: artificial sequence
<220> FEATURE:
<223> OTHER INFORMATION: /note="Description of artificial sequence:
      OCT4 viral PF"

<400> SEQUENCE: 70
ggctctccca tgcattcaaa c                                               21

<210> SEQ ID NO 71
<211> LENGTH: 22
<212> TYPE: DNA
<213> ORGANISM: artificial sequence
<220> FEATURE:
<223> OTHER INFORMATION: /note="Description of artificial sequence:
      OCT4 viral PR"

<400> SEQUENCE: 71
tttatcgtcg accactgtgc tg                                              22

<210> SEQ ID NO 72
<211> LENGTH: 21
<212> TYPE: DNA
<213> ORGANISM: artificial sequence
<220> FEATURE:
<223> OTHER INFORMATION: /note="Description of artificial sequence:
      SOX17 PF"

<400> SEQUENCE: 72
ttcgtgtgca agcctgagat g                                               21

<210> SEQ ID NO 73
<211> LENGTH: 19
<212> TYPE: DNA
<213> ORGANISM: artificial sequence
<220> FEATURE:
<223> OTHER INFORMATION: /note="Description of artificial sequence:
      SOX17 PR"

<400> SEQUENCE: 73
gtcggacacc accgaggaa                                                  19

<210> SEQ ID NO 74
<211> LENGTH: 20
<212> TYPE: DNA
<213> ORGANISM: artificial sequence
<220> FEATURE:
<223> OTHER INFORMATION: /note="Description of artificial sequence:
      SOX2 PF"

<400> SEQUENCE: 74
tggcgaacca tctctgtggt                                                 20

<210> SEQ ID NO 75
```

```
<211> LENGTH: 20
<212> TYPE: DNA
<213> ORGANISM: artificial sequence
<220> FEATURE:
<223> OTHER INFORMATION: /note="Description of artificial sequence:
      SOX2 PR"

<400> SEQUENCE: 75
ccaacggtgt caacctgcat                                                   20

<210> SEQ ID NO 76
<211> LENGTH: 25
<212> TYPE: DNA
<213> ORGANISM: artificial sequence
<220> FEATURE:
<223> OTHER INFORMATION: /note="Description of artificial sequence:
      TDGF1 (Cripto) PF"

<400> SEQUENCE: 76
gggatacagc acagtaagga gctaa                                             25

<210> SEQ ID NO 77
<211> LENGTH: 20
<212> TYPE: DNA
<213> ORGANISM: artificial sequence
<220> FEATURE:
<223> OTHER INFORMATION: /note="Description of artificial sequence:
      TDGF1 (Cripto) PR"

<400> SEQUENCE: 77
cacaaaagga ccccagcatg                                                   20

<210> SEQ ID NO 78
<211> LENGTH: 20
<212> TYPE: DNA
<213> ORGANISM: artificial sequence
<220> FEATURE:
<223> OTHER INFORMATION: /note="Description of artificial sequence:
      ZNF206 PF"

<400> SEQUENCE: 78
tcaccatggc cagaggagag                                                   20

<210> SEQ ID NO 79
<211> LENGTH: 20
<212> TYPE: DNA
<213> ORGANISM: artificial sequence
<220> FEATURE:
<223> OTHER INFORMATION: /note="Description of artificial sequence:
      ZNF206 PR"

<400> SEQUENCE: 79
gcaggccacg ccttattctc                                                   20

<210> SEQ ID NO 80
<211> LENGTH: 23
<212> TYPE: DNA
<213> ORGANISM: artificial sequence
<220> FEATURE:
<223> OTHER INFORMATION: /note="Description of artificial sequence:
      ZNF589 PF"

<400> SEQUENCE: 80
tcgggtggct aaattacatc cag                                               23

<210> SEQ ID NO 81
<211> LENGTH: 22
```

```
<212> TYPE: DNA
<213> ORGANISM: artificial sequence
<220> FEATURE:
<223> OTHER INFORMATION: /note="Description of artificial sequence:
      ZNF589 PR"

<400> SEQUENCE: 81
cccaagggag taaggcaaac tg                                              22

<210> SEQ ID NO 82
<211> LENGTH: 30
<212> TYPE: DNA
<213> ORGANISM: artificial sequence
<220> FEATURE:
<223> OTHER INFORMATION: /note="Description of artificial sequence:
      OCT4 outer PF"

<400> SEQUENCE: 82
gaggatagga atttaagatt agtttgggta                                      30

<210> SEQ ID NO 83
<211> LENGTH: 30
<212> TYPE: DNA
<213> ORGANISM: artificial sequence
<220> FEATURE:
<223> OTHER INFORMATION: /note="Description of artificial sequence:
      OCT4 outer PR"

<400> SEQUENCE: 83
aaatccccca cacctcaaaa cctaacccaa                                      30

<210> SEQ ID NO 84
<211> LENGTH: 31
<212> TYPE: DNA
<213> ORGANISM: artificial sequence
<220> FEATURE:
<223> OTHER INFORMATION: /note="Description of artificial sequence:
      OCT4 inner PF"

<400> SEQUENCE: 84
gaggttggag taggaaggat tgttttggtt t                                    31

<210> SEQ ID NO 85
<211> LENGTH: 30
<212> TYPE: DNA
<213> ORGANISM: artificial sequence
<220> FEATURE:
<223> OTHER INFORMATION: /note="Description of artificial sequence:
      OCT4 inner PR"

<400> SEQUENCE: 85
cccccctaac ccatcacctc caccacctaa                                      30

<210> SEQ ID NO 86
<211> LENGTH: 30
<212> TYPE: DNA
<213> ORGANISM: artificial sequence
<220> FEATURE:
<223> OTHER INFORMATION: /note="Description of artificial sequence:
      OCT4 inner unconverted PF"

<400> SEQUENCE: 86
gaggctggag cagaaggatt gctttggccc                                      30

<210> SEQ ID NO 87
<211> LENGTH: 30
<212> TYPE: DNA
```

```
<213> ORGANISM: artificial sequence
<220> FEATURE:
<223> OTHER INFORMATION: /note="Description of artificial sequence:
      OCT4 inner unconverted PR"

<400> SEQUENCE: 87
cccccctggc ccatcacctc caccacctgg                                     30

<210> SEQ ID NO 88
<211> LENGTH: 29
<212> TYPE: DNA
<213> ORGANISM: artificial sequence
<220> FEATURE:
<223> OTHER INFORMATION: /note="Description of artificial sequence:
      NANOG outer PF"

<400> SEQUENCE: 88 ttagtttta gagtagttgg gattataga                                       29

<210> SEQ ID NO 89
<211> LENGTH: 30
<212> TYPE: DNA
<213> ORGANISM: artificial sequence
<220> FEATURE:
<223> OTHER INFORMATION: /note="Description of artificial sequence:
      NANOG outer PR"

<400> SEQUENCE: 89
ataataacat aaaacaacca actcaatcca                                     30

<210> SEQ ID NO 90
<211> LENGTH: 25
<212> TYPE: DNA
<213> ORGANISM: artificial sequence
<220> FEATURE:
<223> OTHER INFORMATION: /note="Description of artificial sequence:
      NANOG inner PF"

<400> SEQUENCE: 90
tggttaggtt ggttttaaat ttttg                                          25

<210> SEQ ID NO 91
<211> LENGTH: 26
<212> TYPE: DNA
<213> ORGANISM: artificial sequence
<220> FEATURE:
<223> OTHER INFORMATION: /note="Description of artificial sequence:
      NANOG inner PR"

<400> SEQUENCE: 91
aacccaccct tataaattct caatta                                         26

<210> SEQ ID NO 92
<211> LENGTH: 25
<212> TYPE: DNA
<213> ORGANISM: artificial sequence
<220> FEATURE:
<223> OTHER INFORMATION: /note="Description of artificial sequence:
      NANOG inner unconverted PF"

<400> SEQUENCE: 92
tggccaggct ggtttcaaac tcctg                                          25

<210> SEQ ID NO 93
<211> LENGTH: 26
<212> TYPE: DNA
<213> ORGANISM: artificial sequence
```

-continued

```
<220> FEATURE:
<223> OTHER INFORMATION: /note="Description of artificial sequence:
      NANOG inner unconverted PR"

<400> SEQUENCE: 93
gacccaccct tgtgaattct cagtta                                          26
```

GENERATION OF INDUCED PLURIPOTENT STEM (IPS) CELLS

CROSS REFERENCE TO RELATED APPLICATIONS

This application is Continuation of U.S. patent application Ser. No. 12/993,890, filed Dec. 21, 2010, entitled, "GENERATION OF INDUCED PLURIPOTENT STEM (iPS) CELLS," which is a 35 U.S.C. §371 U.S. National Phase Entry of International Application No. PCT/EP2009/003735 filed May 26, 2009, which designates the U.S., and which claims the benefit of priority of European Application No. 080009651.4 filed May 27, 2008, and of U.S. Provisional Application No. 61/166,689 filed Apr. 3, 2009, the contents of which are each incorporated herein by reference in its entirety.

REFERENCE TO SEQUENCE LISTING

The present application is being filed along with a Sequence Listing in electronic format. The Sequence Listing file entitled 20071001USCONSEQLST.txt, was created on Apr. 21, 2015 and is 58,716 bytes in size. The information in electronic format of the Sequence Listing is incorporated herein by reference in its entirety.

The present invention relates to a method of generating an induced pluripotent stem (iPS) cell comprising the step of introducing into a target cell one or two coding sequences each giving rise upon transcription to a factor that contributes to the reprogramming of said target cell into an induced pluripotent stem cell and selected from Oct3/4 or a factor belonging to the Myc, Klf and Sox families of factors, wherein the target cell endogenously expresses at least the factors that are not encoded by the coding sequences to be introduced and selected from Oct3/4 or factors belonging to the Myc, Klf and Sox families of factors, and wherein the cell resulting from the introduction of the one or two coding sequences expresses the combination of factor Oct3/4 and at least one factor of each family of factors selected from the group of Myc, Klf and Sox. Furthermore, the present invention relates to an induced pluripotent stem cell generated by the method of the invention and a method of identifying a compound that contributes to the reprogramming of a target cell into an induced pluripotent stem cell. Also, a method of generating a transgenic non-human animal and a composition comprising an iPS cell generated by the method of the present invention for gene therapy, regenerative medicine, cell therapy or drug screening are envisaged.

Several documents are cited throughout the text of this specification. The disclosure content of the documents cited herein (including manufacturer's specifications, instructions, etc.) is herewith incorporated by reference.

Pluripotent stem cells like embryonic stem (ES) cells are hallmarked by their ability to self-renew and differentiate into a wide variety of cell types. ES cells can be differentiated in vitro into specialized cell lineages of all three embryonic germ layers—ectodermal, mesodermal and endodermal—in the presence of physical inducing and biological inducing factors. So far, many promising studies have shown the therapeutic potential of differentiated derivatives of ESCs in ameliorating a range of disease in animal models. As a result, pluripotent stem cells have enormous potential for use in tissue engineering and transplantation therapy. If these cells can be induced to differentiate into a particular cell type, they may provide an almost unlimited source of cells for transplantation for the treatment of many devastating degenerative diseases such as diabetes, Parkinson's disease and Alzheimer's disease (Biswas et al., 2007; Kim et al., 2007; Zimmermann et al., 2007).

Only recently, it has been shown that somatic cells may be genetically modified to redifferentiate into a state that is in terms of pheno- and genotype as well as pluripotency similar to ES cells (Takahashi and Yamanaka, 2006; Okita et al., 2007; Wernig et al., 2007). The so-called "reprogramming" of somatic cells is a valuable tool to understand the mechanisms of regaining pluripotency and further opens up the possibility to generate patient-specific pluripotent stem cells. Reprogramming of mouse and human somatic cells into pluripotent stem cells, designated as induced pluripotent stem (iPS) cells, has been possible with the expression of the transcription factor quartet Oct4, Sox2, c-Myc, and Klf4.

Presently, although it is widely acknowledged that iPS cells have a great potential for medical applications such as, e.g., patient-specific regenerative cell therapy, the currently employed methods to generate iPS cells prevent their use in the medical field. Specifically, the retroviral vectors used to introduce and express the combination of several reprogramming factors randomly integrate into the genome in multiple copies, preferably into the vicinity or into active endogenous genes and hence may cause activating or inactivating mutations of cancer or tumor suppressor genes, respectively. Thus, the generation of iPS cells using a method that minimizes the degree of modification of the target cell's genome may boost the clinically safe application of this approach.

Accordingly, the present invention relates in a first embodiment to a method of generating an induced pluripotent stem (iPS) cell comprising the step of introducing into a target cell one or two coding sequences each giving rise upon transcription to a factor that contributes to the reprogramming of said target cell into an induced pluripotent stem cell and selected from Oct3/4 or a factor belonging to the Myc, Klf and Sox families of factors, wherein the target cell endogenously expresses at least the factors that are not encoded by the coding sequences to be introduced and selected from Oct3/4 or factors belonging to the Myc, Klf and Sox families of factors, and wherein the cell resulting from the introduction of the one or two coding sequences expresses the combination of factor Oct3/4 and at least one factor of each family of factors selected from the group of Myc, Klf and Sox.

An "induced pluripotent stem (iPS) cell" is a cell that exhibits characteristics similar to embryonic stem cells (ESCs). Said characteristics include, for example, unlimited self renewal in vitro, a normal karyotype, a characteristic gene expression pattern including stem cell marker genes like Oct3/4, Sox2, Nanog, alkaline phosphatase (ALP) and stem cell-specific antigen 3 and 4 (SSEA3/4), and the capacity to differentiate into specialized cell types (Hanna, J., et al. (2007). Science 318(5858): 1920-3; Meissner, A., et al. (2007). Nat Biotechnol 25(10): 1177-81; Nakagawa, M., et al. (2007). Nat Biotechnol.; Okita, K., et al. (2007). Nature 448(7151): 313-7; Takahashi, K., et al. (2007 Cell 131(5): 861-72; Wernig, M., et al. (2007). Nature 448(7151): 318-24; Yu, J., et al. (2007). Science 318(5858): 1917-20; Park, I. H., et al. (2008). Nature 451(7175): 141-6). The state of the art generation of iPS cells from fibroblast cultures has been described in Takahashi, Okita, Nakagawa, Yamanaka (2007) Nature Protocols 2(12). The pluripotency of murine iPS cells can tested, e.g., by in vitro differentiation into neural, glia and cardiac cells and the production of germline chimaeric mice through blastocyst injection. Human iPS cells lines can be analyzed through in vitro differentiation into neural, glia and cardiac cells and their in vivo differentiation capacity can be tested by injection into immunodeficient SCID mice and the characterisation of resulting tumors as teratomas.

iPS cells can generally be evaluated and classified according to the following cellular biological properties:

Morphology: iPS cells are morphologically similar to embryonic stem cells (ESCs). Each cell has a round shape, large nucleolus and scant cytoplasm. Colonies of iPS cells are also similar to that of ESCs. Human iPS cells form sharp-edged, flat, tightly-packed colonies similar to hESCs whereas mouse iPS cells form the colonies similar to mESCs, less flatter and more aggregated colonies than that of hESCs.

Growth properties: Doubling time and mitotic activity are cornerstones of ESCs, as stem cells must self-renew as part of their definition. iPS cells are mitotically active, actively self-renewing, proliferating, and dividing at a rate equal to ESCs.

Stem cell markers: iPS cells express cell surface antigenic markers expressed on ESCs. Human iPSCs express the markers specific to hESC, including SSEA-3, SSEA-4, TRA-1-60, TRA-1-81, TRA-2-49/6E, and Nanog. Mouse iPS cells express SSEA-1 but not SSEA-3 nor SSEA-4, similarly to mESCs.

Stem Cell Genes: iPS cells express genes expressed in undifferentiated ESCs, including, e.g., Oct3/4, Sox2, Nanog, GDF3, REX1, FGF4, ESG1, DPPA2, DPPA4, and hTERT.

Telomerase activity: Telomerases are necessary to sustain cell division unrestricted by the Hayflick limit of ~50 cell divisions. hESCs express high telomerase activity to sustain self-renewal and proliferation, and iPS cells also demonstrate high telomerase activity and express hTERT (human telomerase reverse transcriptase), a necessary component in the telomerase protein complex.

Pluripotency: iPS cells are capable of differentiation in a fashion similar to ESCs into fully differentiated tissues. For example, iPS cells injected into immunodeficient mice spontaneously form teratomas after nine weeks. Teratomas are tumors of multiple lineages containing tissue derived from the three germ layers endoderm, mesoderm and ectoderm; this is unlike other tumors, which typically are of only one cell type. Teratoma formation is a landmark test for pluripotency. Further, hESCs in culture spontaneously form ball-like embryo-like structures termed "embryoid bodies", which consist of a core of mitotically active and differentiating hESCs and a periphery of fully differentiated cells from all three germ layers. iPS cells also form embryoid bodies and have peripheral differentiated cells. Blastocyst Injection: hESCs naturally reside within the inner cell mass (embryoblast) of blastocysts, and in the embryoblast, differentiate into the embryo while the blastocyst's shell (trophoblast) differentiates into extraembryonic tissues. The hollow trophoblast is unable to form a living embryo, and thus it is necessary for the embryonic stem cells within the embryoblast to differentiate and form the embryo. iPS cells can be injected by micropipette into a trophoblast, and the blastocyst is transferred to recipient females. Chimeric living mouse pups can thus be created, i.e. mice with iPS cell derivatives incorporated all across their bodies with a varying degree of chimerism.

Promoter demethylation: Methylation is the transfer of a methyl group to a DNA base, typically the transfer of a methyl group to a cytosine molecule in a CpG site (adjacent cytosine/guanine sequence). Widespread methylation of a gene interferes with expression by preventing the activity of expression proteins or recruiting enzymes that interfere with expression. Thus, methylation of a gene effectively silences it by preventing transcription. Promoters of pluripotency-associated genes, including for example Oct3/4, Rex1, and Nanog, are demethylated in iPS cells, demonstrating their promoter activity and the active promotion and expression of pluripotency-associated genes in iPSCs.

Histone demethylation: Histones are compacting proteins that are structurally localized to DNA sequences that can effect their activity through various chromatin-related modifications. H3 histones associated with, e.g., Oct3/4, Sox2, and Nanog are demethylated, indicating the expression of Oct3/4, Sox2, and Nanog.

The term "introducing" as used in accordance with the present invention relates to the process of bringing the coding sequences into the target cell and subsequently incorporation of said coding sequences into the genomic DNA of the target cell. This process is generally known as stable transfection and methods for stable transfection are well-known to the person skilled in the art and described, e.g., in Bonetta, L., (2005), Nature Methods 2, 875-883. Due to the low rate of reprogramming events taking place in transfected cells it is advantageous to rely on an efficient stable transfection method. Hence, the coding sequences are preferably introduced into a target cell by a method achieving high transfection/infection efficiency. For example, transfection/infection efficiencies of at least 30%, at least 50%, or at least 80% are preferred. Suitable methods include, for example, lipofection, electroporation, nucleofection, magnetofection or viral vector infection. Preferably, retroviral vectors are used to achieve stable transfection of the target cells as said vectors not only mediate efficient entry of the coding sequences into the target cell but also their integration into the genomic DNA of the target cell. Retroviral vectors have shown to be able to transduce a wide range of cell types from different animal species, to integrate genetic material carried by the vector into target cells, to express the transduced coding sequences at high levels, and, advantageously, retroviral vectors do not spread or produce viral proteins after infection. Suitable retroviral vector systems are well-known to the person skilled in the art such as, e.g., retroviral vectors with the MoMuLV LTR, the MESV LTR, lentiviral vectors with various internal promoters like the CMV promoter, preferably with enhancer/promoter combinations that show silencing of transgene expression in embryonic/pluripotent cells. Episomal vector systems like adenovirus vectors, other non-integrating vectors, episomally replicating plasmids could also be used. Preferably, the retroviral MX vector system is used in the method of the invention (Kitamura et al., (2003), Exp Hematol., 31(11): 1007-1014).

Target cells to be used in the method of the invention can be derived from existing cells lines or obtained by various methods including, for example, obtaining tissue samples in order to establish a primary cell line. Methods to obtain samples from various tissues and methods to establish primary cell lines are well-known in the art (see e.g. Jones and Wise, Methods Mol Biol. 1997). Suitable somatic cell lines may also be purchased from a number of suppliers such as, for example, the American tissue culture collection (ATCC), the German Collection of Microorganisms and Cell Cultures (DSMZ) or PromoCell GmbH, Sickingenstr. 63/65, D-69126 Heidelberg. In accordance with the method of the invention, a suitable target cell endogenously expresses factors selected from Oct3/4 or factors belonging to the Myc, Klf and Sox families of factors, wherein said factors in combination with exogenously introduced factors selected from the complementary set of factors, i.e. Oct3/4 or factors belonging to the Myc, Klf and Sox families of factors, are capable to reprogram a non-pluripotent target cell into an iPS cell. The cell resulting from the introduction of the one or two coding sequences expresses the combination of factor Oct3/4 and at least one factor of each family of factors selected from the group of Myc, Klf and Sox. The person skilled in the art is well-aware of methods to determine whether at least two of the above-described factors are endogenously expressed in a target cell. Such methods include, e.g., western blotting, realtime-PCR or intercellular stainings. The skilled person is further capable to realize without further ado which exogenous factor(s) are needed to complement the set of endogenously expressed factors in order to generate a cell that expresses the combination of Oct3/4 and at least one factor of each family of factors selected from the group of Myc, Klf and Sox to initiate reprogramming of the target cell into an iPS cell. The cell into which the coding sequence(s) in expressible form have been introduced thus expresses a set of factors consisting of Oct3/4 and at least one factor of each family of factors selected from the group of Myc, Klf and Sox.

The invention also encompasses embodiments where a coding sequence is introduced that is already endogenously present in the target cell. This may be effected, e.g., in cases where the endogenous coding sequence is expressed only at a low level with the effect that the corresponding factor does not or not sufficiently contribute to the reprogramming of the target cell.

The term "coding sequence" relates to a nucleotide sequence that upon transcription gives rise to the encoded product. The transcription of the coding sequence in accordance with the present invention can readily be effected in connection with a suitable promoter. Preferably, the coding sequence corresponds to the cDNA sequence of a gene that gives rise upon transcription to a factor that contributes to the reprogramming of a target cell into an induced pluripotent stem cell, wherein the reprogramming factors in accordance with the method of the invention are selected from Oct3/4 or factors belonging to the Myc, Klf and Sox families of factors.

A "factor that contributes to the reprogramming of a target cell into an induced pluripotent stem cell" relates to a factor that is capable of contributing to the induction of the reprogramming of target cells into induced pluripotent stem cells, wherein the factor is selected from Oct3/4 and factors belonging to the Myc, Klf and Sox families of factors. Such reprogramming factors include, for example, Oct3/4, Sox2, Sox1, Sox3, c-Myc, n-Myc, I-Myc, Klf1, Klf2, Klf4, Klf5, and the like, or mutants thereof with retained reprogramming capabilities. Said contribution to the reprogramming may be in the form of, for example, changing the methylation pattern of a cell to one similar to an embryonic stem cell, shifting the expression profile of a cell towards the expression profile of an embryonic stem cell or affecting conformation of the aggregated nuclear DNA by modulating the histone binding similar to that observed in an embryonic stem cell wherein each of said changes may be effected either alone or in combination by a suitable reprogramming factor. Apart from the above-recited factors, the skilled person is aware of methods to identify further suitable reprogramming factors such as, e.g., bisulphite genomic sequencing, RT-PCR, real-time PCR, microarray analysis, karyotype analysis, teratoma formation, alkaline phosphatase staining, all of which are well-known to the person skilled in the art and are, for example described in Okita, K., et al. (2007), Nature 448(7151): 313-7; Park, I. H., et al. (2008), Nature 451(7175): 141-6; Takahashi, K., et al. (2007), Cell 131(5): 861-72; Wernig, M., et al. (2007), Nature 448(7151): 318-24; Takahashi, K. et al. (2007), Nat Protoc 2(12): 3081-9; or Hogan, B., et al. (1994), "Manipulating the Mouse Embryo: A Laboratory Manual", Cold Spring Harbour Press.

Oct3/4 belongs to the family of octamer ("Oct") transcription factors, and plays a role in maintaining pluripotency. The absence of Oct3/4 in cells normally expressing Oct3/4, such as blastomeres and embryonic stem cells, leads to spontaneous trophoblast differentiation. Thus, the presence of Oct3/4 contributes to the pluripotency and differentiation potential of embryonic stem cells. Various other genes in the "Oct" family, including Oct1 and Oct6, fail to elicit induction, thus demonstrating the exclusiveness of Oct3/4 to the induction process. The term "Oct4" is used herein interchangeably with the term "Oct3/4".

The Sox family of genes is associated with maintaining pluripotency similar to Oct3/4, although it is associated with multipotent and unipotent stem cells in contrast to Oct3/4, which is exclusively expressed in pluripotent stem cells. Klf4 of the Klf family of genes was initially identified as a factor for the generation of mouse iPS cells and was demonstrated as a factor for generation of human iPS cells.

The genes belonging to the Myc family are proto-oncogenes implicated in cancer. It was demonstrated that c-Myc is a factor implicated in the generation of mouse iPS cells and that it was also a factor implicated in the generation of human iPS cells. Introduction of the "Myc" family of genes into target cells for the generation of iPS cells is troubling for the eventuality of iPS cells as clinical therapies, as 25% of mice transplanted with c-Myc-induced iPS cells developed lethal teratomas. N-Myc and I-Myc have been identified to replace c-myc with similar efficiency.

The term "reprogramming" as used in accordance with the present invention relates to the process of changing the geno- and phenotypical profile of a cell that results in a cell that is geno- and/or phenotypically similar to an embryonic stem cell. Said changes comprise, for example, changes in the methylation pattern, shifts in the expression profile or conformational changes of the aggregated nuclear DNA as described herein above.

The above applies mutatis mutandis to other embodiments described herein below.

The method of the invention is based upon the surprising finding that it is possible to obtain iPS cells by the introduction of only two reprogramming factors. Prior to this finding the dogma of the prior art was that viable iPS cells which are functional in in vivo experiments, i.e. capable of contributing to the three germlayers, could only successfully be generated by introducing at least three, but more effectively by introducing a combination of four reprogramming factors.

Exemplarily, it was demonstrated that murine neural stem cells (NSCs) could be reprogrammed by introducing a combination of four (4F), three (3F) and only two (2F) reprogramming factors as well as only one reprogramming factor using the retroviral MX vector system. The NSCs were established from adult OG2/Rosa26 heterozygous transgenic mice brain (Ryan, A. K. & Rosenfeld, M. G., Genes Dev 11, 1207-25 (1997); Do, J. T. & Scholer, H. R., Stem Cells 22, 941-9 (2004); Pollard, S. M., Conti, L., Sun, Y., Goffredo, D. & Smith, A., Cereb Cortex 16 Suppl 1, i112-20 (2006)), expressing GFP under the control of the Oct4 promoter (Oct4-GFP) and the lacZ transgene from the constitutive Rosa26 locus.

First observed were GFP+ colonies in NSC cultures infected with Oct4 and Klf4 (2F OK) and 1-2 weeks later in those infected with Oct4 and c-Myc (2F OM) (Table 1).

TABLE 1

Overview of the applied combinations of reprogramming factors, timing of GFP colony formation, and establishment of iPS cell lines

| Transfected factors | Timing of GFP-positive colonies | Establishment of iPS cell line |
|---|---|---|
| OK | 2-3 weeks | + |
| OM | 3-4 weeks | + |

The 2F OM iPS cells were further analyzed and showed an ESC-like expression pattern as well as contributing to the three germ layers in teratomas.

2F OK iPS cells were compared with 4F (generated using standard approach of introducing 4 reprogramming factors to generate iPS cells) iPS cells and ESCs. On day 14 post-infection, 5 GFP+ colonies were dissociated and propagated under ESC culture conditions (FIG. 1c, f), yielding 3 (i.e. 60%) 2F OK iPS cell clones (B-2, D-7 and F-4) that were morphologically indistinguishable from ESCs (FIG. 1d, g). No colonies had formed from NSCs infected with control virus (MX) (FIG. 1e, h). The reprogramming efficiencies were estimated from the number of Oct4-GFP+ colonies and transduction rates with MX-GFP control virus on NSCs for the 2F OK iPS and 4F iPS by time course (FIG. 1i, j). Thereby a reprogramming efficiency of 3.6% for 4F reprogramming of NSCs and 0.11% for the two factors approach was calculated, what is comparable to reprogramming of fibroblasts with selection (below 0.08%, Takahashi, K. & Yamanaka, S., Cell 126, 663-76 (2006); Okita, K., Ichisaka, T. & Yamanaka, S., Nature 448, 313-7 (2007); Wernig, M. et al., Nature 448, 318-24 (2007)) and without selection (0.5%; Meissner, A., Wernig, M. & Jaenisch, R., Nat Biotechnol 25, 1177-81 (2007)) (FIG. 1j). Transduction with all 4 factors had a positive impact on the timing and number of GFP+ colonies. Integration of the viral transgenes was confirmed by genotyping PCR. The viral transgenes of all 4 factors were detected in 4F iPS cells, while 2F OK iPS cells only contained the Oct4 and Klf4 transgenes.

2F OK iPS cells stained positive for SSEA-1 and alkaline phosphatase, and exhibited ES cell marker genes expression patterns similar to 4F iPS cells and ESCs (FIG. 2a). qRT-PCR results demonstrated that expression of endogenous Oct4, Sox2, c-Myc, and Klf4 in 2F OK iPS cells was comparable to ESCs, and the silencing of the viral transcripts in 2F OK iPS cells with a 1000-fold reduction after 30 days. 2F iPS global gene expression also clusters close to ESCs and 4F iPS (FIG. 2b). Scatter plots of DNA microarray analyses demonstrated a higher similarity between 2F iPS cells and ESCs than between 2F iPS cells and NSCs (FIG. 2c, d). Thus, 2F iPS cells (clone F-4) seemed to be very similar to mouse ESCs at the global transcription level.

The differentiation ability of 2F OK iPS cells was confirmed by in vitro differentiation into embryoid bodies (EBs). These cells expressed the ectoderm (Tuj1), endoderm (α-fetoprotein), and mesoderm marker Flk1 (expressed by beating cells mimicking cardiomyocytes) (FIG. 3a). Teratomas contained derivatives of all three germ layers (FIG. 3b), and expressed markers of the three germ layer. No teratoma had formed from donor cells (NSCs). These data demonstrate that 2F OK iPS cells exhibit a pluripotent phenotype in in vitro and in vivo.

To investigate their developmental potential, 2F OK iPS cells were aggregated with 8-cell-stage embryos. iPS cells had contributed to the formation of the inner cell mass in developing blastocysts (FIG. 4a). After transferring aggregated blastocysts into pseudopregnant females, 16 live embryos were obtained on E13.5, of which 2 embryos showed germ cell contribution in the foetal gonads, judged from Oct4-GFP expression (FIG. 4b). X-gal staining (visualising the NSC donor cells that carry the Rosa β-geo26 (lacZ) transgene) of embryonic tissue from whole embryos revealed that in the resulting chimeras, 2F OK iPS cells contributed to the development of all three germ layers (FIG. 4c, e). The strictest test for developmental potency tetraploid (4N) embryo aggregation (n=122) resulted in 2 dead (arrested) embryos at E13.5 (FIG. 4d). This is within the normal rate for 4N embryo aggregation and was not related to deficient pluripotency of the introduced cells. These data demonstrate that iPS cells can give rise to all of the tissues of a late-stage embryo. In diploid (2N) aggregation, PCR genotyping showed that 2 out of 13 chimeras were positive for the Oct4-GFP allele of the donor cell (FIGS. 4f and g (top panel)). To assess whether 2F OK iPS cells can contribute to the germline, chimeras were mated with CD-1 females. Two out of 12 pups had a Oct4-GFP allele and 1 out of 12 mice had a lacZ allele. Since the donor cells are derived from a heterogeneous mouse (Oct4+/−Rosa26+/−), they also have the Oct4 and Klf4 transgenes (FIG. 4g (bottom panel)). No tumour formation was observed from adult chimeras and F1 mice by the age of 17 weeks and 3 weeks respectively. This finding indicates that 2F OK iPS cells can contribute the full term development of chimera, resulting in a next generation (F1) of viable pups and thus suggests that the iPS cells have a similar developmental property like ESCs.

As described in detail in Example 9 below, the inventors were able to also demonstrate conversion of human cells into pluripotent stem cells by the introduction of two or only one reprogramming factor. Said reprogramming factors were Oct4 or Oct4 and Klf4.

In conclusion, the above findings demonstrate the successful generation of iPS cells using two reprogramming factors or only one reprogramming factor. The advantage of the method of the invention lies in the use of only two or even only one retroviral vector for stable transfection of one or two reprogramming factors. The possibility of inducing iPS cells with a reduced number of retroviral vectors as compared to prior art approaches presents a major step towards the minimization of genetic modulation of the initial cell population to be reprogrammed. Accordingly, the risk of formation of aberrant and tumourigenic cells is significantly decreased, hence allowing the generation of iPS cells suitable for therapeutic purposes, inter alia.

In a preferred embodiment of the method of the invention, the factors belonging to the factor families of Myc, Klf and Sox and endogenously expressed by or encoded by the coding sequences to be introduced into the target cell are selected from the group consisting of l-Myc, n-Myc, c-Myc, Klf1, Klf2, Klf4, Klf15, Sox1, Sox2, Sox3, Sox15 and Sox18.

The coding sequence of, for example, murine Oct3/4, Sox2, c-Myc, and Klf4 can be found in SEQ ID NOs: 1, 5, 9 and 13, respectively. The protein sequence of murine Oct3/4, Sox2, c-Myc and Klf4 can be found in SEQ ID NOs: 2, 6, 10 and 14, respectively. The coding sequence of human Oct3/4, Sox2, c-Myc and Klf4 can be found in SEQ ID NOs: 3, 7, 11 and 15, respectively. The protein sequence of human Oct3/4, Sox2, c-Myc and Klf4 can be found in SEQ ID NOs: 4, 8, 12 and 16, respectively. The skilled person is in the position to determine the coding sequences of reprogramming factors for any target species using methods well-known in the art. For example, he can retrieve data relating to sequence and function from databases such as, for example, the databases maintained by the National Center for Biotechnology Information (NCBI) and accessible via the World Wide Web under http://www.ncbi.nlm.nih.gov/. Further, databases for comparative genomics include without limitation, a database maintained also by the NCBI at http://www.dcode.org/, a database for protein annotations for all completely sequenced organisms accessible at http://supfam.org/SUPERFAMILY/, a database comprising genome information for various species accessible at http://www.cbs.dtu.dk/services/GenomeAtlas/, or a database comprising gene clusters accessible at http://phigs.jgi-psf.org/. Said databases allow the skilled person to identify coding sequences for reprogramming factors in other species starting from the sequences known for mice and humans by, for example, performing cross-species sequence alignments to identify homologous genes.

Several, only recently published scientific articles (Hanna, J., et al. (2007). Science 318(5858): 1920-3; Meissner, A., et al. (2007). Nat Biotechnol 25(10): 1177-81; Nakagawa, M., et al. (2007). Nat Biotechnol.; Okita, K., et al. (2007), Nature 448(7151): 313-7; Takahashi, K., et al. (2007), Cell 131(5): 861-72; Wernig, M., et al. (2007). Nature 448(7151): 318-24; Yu, J., et al. (2007). Science 318(5858): 1917-20; Park, I. H., et al. (2008). Nature 451(7175): 141-6) have shown that transcription factors belonging to the Oct, Sox, Klf and Myc families are capable of contributing to the induction of reprogramming in murine as well as human somatic cells.

In another preferred embodiment, the target cell does not endogenously express one of the factors encoded by the one or two coding sequences to be introduced into said target cell.

Methods of assessing endogenous expression of factors are well-known to the skilled person and described elsewhere in this specification. In order to generate iPS cells in accordance with the method of the invention the target cell may not endogenously express one of the factors encoded by the one or two coding sequences that are to be introduced into the target cell. For example, it could be demonstrated that Oct3/4 was not expressed in murine neural stem cells as target cells, whereas Sox2, Klf4 and c-Myc were endogenously expressed. Exogenous introduction of Oct3/4 and subsequent expression was sufficient to complement the quartet of reprogramming factors and induce generation of iPS cells.

In another preferred embodiment, the target cell is a multipotent stem cell.

Multipotent stem cells can give rise to several other cell types, but those types are limited in number. This is in stark contrast to pluripotent stem cells being capable of differentiating into any cell type. An example of a multipotent stem cell is a hematopoietic cell, found e.g. in bone marrow, cord blood or circulation, that can develop into several types of blood cells, but cannot develop into other types of cells. Another example of multipotent cells are neural stem cells. Multipotent cells are particularly suitable as reprogramming target cells, since they already have reprogramming factors upregulated.

In more preferred embodiment, the multipotent stem cell is an ectodermal cell.

The ectoderm is the outermost of the three primary germ cell layers (the other two being the mesoderm and endoderm) that make up the very early embryo. It differentiates to give rise to many important tissues and structures including the outer layer of the skin and its appendages (the sweat glands, hair, and nails), the teeth, the lens of the eye, parts of the inner ear, neural tissue, brain, and spinal cord. Ectodermal cells as multipotent stem cells are particularly suitable as target cells, since ectodermal cells like neural stem cells already endogenously express reprogramming factors.

In another preferred embodiment, the target cell is a neural stem cell (NSC).

Neural stem cells exist not only in the developing mammalian nervous system but also in the adult nervous system of all mammalian organisms, including humans. Neural stem cells can also be derived from more primitive embryonic stem cells. The location of the adult stem cells and the brain regions to which their progeny migrate in order to differentiate remain unresolved, although the number of viable locations is limited in the adult (for a review see Gage, 2000). Neural stem cells are particularly suitable as target cells as they already endogenously express reprogramming factors.

In a more preferred embodiment, the coding sequence to be introduced encodes the factor Oct3/4.

As outlined herein above and demonstrated in the Examples below, the introduction of Oct3/4 alone into a neural stem cell was sufficient to generate iPS cells. As c-Myc increases tumourigenicity in chimera pups (Okita, K., Ichisaka, T. & Yamanaka, S., Nature 448, 313-7 (2007)), the recent studies demonstrating iPS cell generation without the c-Myc retroviral integration (Nakagawa, M. et al., Nat Biotechnol 26, 101-106 (2008); Wernig, M., Meissner, A., Cassady, J. P. & Jaenisch, R., Cell Stem Cells 2, 11-12 (2008)) present a significant improvement. However, the possibility of inducing iPS cells without c-Myc as presented in this embodiment in combination with the reduced number of retroviral vectors is a major step towards the minimization of genetic modulation of the initial cell population to be reprogrammed.

The same target cell could also be reprogrammed by the introduction of only two factors. Accordingly, in a different more preferred embodiment, the two coding sequences to be introduced encode factors Oct3/4 and c-Myc or Oct3/4 and Klf4.

In an even more preferred embodiment, the target cell endogenously expresses the factors c-Myc, Klf4 and Sox2.

It could be shown that the target cell when endogenously expressing the above combination of reprogramming factors was amenable to reprogramming upon introduction of one or two exogenous reprogramming factors, such as Oct3/4 alone or Oct3/4 and c-Myc or Oct3/4 and Klf4.

In an even more preferred embodiment, the target cell endogenously expresses the factors c-Myc, Klf4 and Sox2 at levels at least 10-fold lower or at most 10-fold higher as compared to the corresponding expression levels in embryonic stem cells of the same genus as the target cell.

It is advantageous in accordance with the method of the invention when the expression levels of the endogenous reprogramming factors are in a certain range as compared to the expression levels in ESCs of the same genus as the target cell. Preferably, the target cell endogenously expresses the reprogramming factors c-Myc, Klf4 and Sox2 at levels at least 10-fold lower or at most 10-fold higher as compared to the corresponding expression levels of said factors in ESCs. More preferred is the expression of Sox2 about two-fold higher, c-Myc about 10-fold higher and/or Klf4 about 8-fold lower than in ESCs belonging to the same genus as the target cells. The term "about" as used in the context of the present invention refers to an average deviation of maximum +/−20%, preferably +/−10%. Also envisaged is the expression at levels at least 8-, 6-, 5-, 4-, 3- or 2-fold lower or at most 8-, 6-, 5-, 4-, 3- or 2-fold higher or any arbitrary number in-between as compared to said ESCs.

In a more preferred embodiment, the target cell is a murine or a human neural stem cell.

Furthermore, the invention relates to an induced pluripotent stem cell generated by the method of the invention.

Pluripotent stem cells generated by the method of the invention may be useful in a variety of experimental as well as therapeutic settings. For example, the use of the iPS cells, of cells derived therefrom by differentiation or tissues generated from said iPS cells or cells derived therefrom as a therapeuticum or diagnosticum, within gene or cell transplantation treatments, for the identification and validation of genomic targets as well as Drug screening approaches are envisaged.

The culture conditions for iPS cells are the same as established for embryonic stem cells of the corresponding species and are well-known to the person skilled in the art. Generally, cell culture methods, such as, for example, media constituents, marker choice and selection, cell quantification and isolation, are methods well-known in the art and described, for example, in "Practical Cell Culture Techniques", Boulton et Baker (eds), Humana Press (1992), ISBN 0896032140; "Human Cell Culture Protocols", Gareth E. Jones, Humana Press (1996), ISBN 089603335X and exemplarily in the example section. Methods for culturing and maintaining cells in culture are well-known in the art; growth media and other cell culture related material as well as instructions and methods for successful culturing of cells can, for example, be obtained at Sigma-Aldrich or Invitrogen.

Further, the invention relates to a method of identifying a compound that contributes to the reprogramming of a target cell into an induced pluripotent stem cell comprising the steps of: (a) reprogramming a target cell according to the method of the invention, wherein one coding sequence to be introduced is replaced by the compound to be tested; and (b) assessing whether iPS cells are formed in the presence and absence of the compound to be tested, wherein the formation of iPS cells from target cells in which the compound to be tested has been introduced is indicative of the compound contributing to the reprogramming of a target cell into an induced pluripotent stem cell.

In accordance with the invention the compound to be tested may be one or more nucleic acids, such as DNA, cDNA, RNA, dsRNA, siRNA, shRNA, miRNA, proteins, peptides, small molecules (organic or inorganic), chemicals or any combination thereof.

Reprogramming a target cell in accordance with the method of the invention has been described herein-above. Depending on the nature of the compound to be tested the method of the invention may need to be modified as regards the introduction step of the compound into the target cell. For example, if other transcription factors are to be evaluated the corresponding coding sequences may be introduced as described above without modification. In contrast, chemicals or small molecules may be introduced by exogenously adding the respective compound to the cell medium and taking advantage of passive or active cellular uptake mechanisms. The skilled person is well-aware of methods that allow the introduction of any compound to be tested into the cell, preferably into the nucleus, in order to test whether the compound can indeed substitute the factor it replaces and accordingly induce reprogramming of the target cell. Nucleic acids, such as DNA, cDNA, RNA, dsRNA, siRNA, shRNA, miRNA can be introduced by transfection or infection, small molecules (organic or inorganic), chemicals just be penetration throughout the membrane.

The skilled person is well aware of methods to assess whether iPS cells are formed in the presence and absence of the compound to be tested. Criteria for the classification of an iPS cell are known to the skilled person and have been described herein above. Depending on the criteria to be assessed the methods vary and may include, e.g., visual control by microscopy, expression analysis of markers, teratoma formation alone or in combination.

The finding of the invention that cells endogenously expressing a set of factors contributing to the reprogramming of said cell may be complemented by the exogenous addition of further factors resulting in a cell expressing a quartet of reprogramming factors, i.e. Oct3/4 and a factor of each family of factors Myc, Klf and Sox, leading to the induction of reprogramming of the target cell, significantly simplifies the identification of compounds that can replace a factor in the reprogramming process. As only one or two factors have to be introduced instead of three or the entire set of four factors known in the art to generate cells suitable for screening, a considerable reduction of time, costs and experimental difficulties is achieved. Also high throughput screening approaches for novel reprogramming factors will evidently be improved as regards time and efficiency with a reduced set of factors necessary to be introduced.

Also, the invention relates to a method of generating a transgenic non-human animal comprising the steps of: (a) introducing the induced pluripotent stem cell of the invention or generated by the method of the invention into a non-human preimplantation embryo; (b) transferring the embryo of step (a) into the uterus of a female non-human animal; and (c) allowing the embryo to develop and to be born.

The term "transgenic non-human animal" as used in accordance with the invention relates to an animal in which there has been effected a deliberate modification of its genome by methods described herein.

The method of the invention of generating a transgenic non-human animal is preferably carried out according to methods that have been established for generating transgenic non-human animals by the use of embryonic stem cells, however, replacing the embryonic stem cells with iPS cells of the invention. Said methods are well-known in the art (Hogan, B., R. Beddington, et al. (1994), "Manipulating the Mouse Embryo: A Laboratory Manual", Cold Spring Harbour Press; Hanna, J., et al. (2007), Science 318(5858): 1920-3; Meissner, A., et al. (2007), Nat Biotechnol 25(10): 1177-81; Nakagawa, M., et al. (2007), Nat Biotechnol.; Okita, K., et al. (2007), Nature 448(7151): 313-7; Takahashi, K., et al. (2007), Cell 131(5): 861-72; Wernig, M., et al. (2007), Nature 448(7151): 318-24; Yu, J., et al. (2007), Science 318(5858): 1917-20; Park, I. H., et al. (2008), Nature 451(7175): 141-6). In brief, introduction of the iPS cell into a non-human preimplantation embryo, like a morula or a blastocyst, is preferably effected by microinjection into a morula or blastocyst or by aggregation of iPS cells with 8-cell or morula embryos. Said chimaeric embryo is then transferred into the uterus of a pseudopregnant non-human female where it develops into an embryo that is finally born (cf. Example 8).

Generating a transgenic non-human animal line from iPS cells is based on the pluripotence of said iPS cells (i. e., their ability, once injected into a host developing embryo, such as a blastocyst or morula, to participate in embryogenesis and to contribute to the germ cells of the resulting animal). As outlined above, the blastocysts containing the injected iPS cells are allowed to develop in the uteri of pseudopregnant non-human females and are born as chimeras. The resultant transgenic non-human animals are chimeric for cells originating from iPS cells and are backcrossed to wildtype non-human animals and screened for animals carrying only the genetic content of an iPS cell so as to identify transgenic animals homozygous for the combination of DNA segments.

The transgenic non-human animals may, for example, be transgenic mice, rats, hamsters, dogs, monkeys, rabbits, pigs, or cows. Preferably, said transgenic non-human animal is a mouse.

Accordingly, the invention also relates to a transgenic non-human animal generated by the method of the invention.

Finally, the invention relates to a composition comprising an iPS cell generated by the method of the invention for gene therapy, regenerative medicine, cell therapy or drug screening.

A composition as used herein relates to a composition that comprises iPS cells and preferably further constituents that maintain cell viability of said cell. Such constituents are well-known to the skilled person and comprise, for example, cell media constituents. Further, depending on the intended application the composition may comprise additional constituents, for example, constituents facilitating administration to a patient.

A composition comprising the iPS cells of the invention (as well as the iPS cells of the invention per se) can be used in a variety of experimental as well as therapeutic scenarios. The iPS cell of the invention having a comparatively low number of transgenic expression elements and an overall reduced risk of developing into cancerous cells are expected to be beneficial in gene therapy, regenerative medicine, cell therapy or drug screening.

Gene therapy, which is based on introducing therapeutic DNA constructs for correcting a genetic defect into germ line cells by ex vivo or in vivo techniques, is one of the most important applications of gene transfer. Suitable vectors and methods for in vitro or in vivo gene therapy are described in the literature and are known to the person skilled in the art (Davis P B, Cooper M J., AAPS J. (2007), 19; 9(1):E11-7; Li S, Ma Z., Curr Gene Ther. (2001), 1(2):201-26). In accordance with the invention, cells obtained from a patient could, for example, be genetically corrected by methods known in the art and subsequently be reprogrammed into iPS cells having the pheno- and genotype of ES cells, by the method of the invention. This evidences the applicability of iPS cells in gene therapy and/or cell therapy. Regenerative medicine can be used to potentially cure any disease that results from malfunctioning, damaged or failing tissue by either regenerating the damaged tissues in vivo or by growing the tissues and organs in vitro and subsequently implanting them into the patient. The iPS cells of the invention being capable of differentiating into virtually any tissue (ectoderm, mesoderm, endoderm cells) can be used in any aspect of regenerative medicine and hence drastically reduce the need for ES cells.

The iPS cells of the invention can also be used to identify drug targets and test potential therapeutics hence reducing the need for ES cells and in vivo studies. Experimental setups and methods to identify and/or assess effects of a potential drug including, for example, target-site and -specificity, toxicity, bioavailability, are well-known to the person skilled in the art.

Further, the iPS cells may be used to study the prevention and treatment of birth defects or study cell differentiation.

Also, the iPS cells of the invention may be useful in an experimental setting—besides therapeutic applications—to study a variety of aspects related to dedifferentiation when inducing reprogramming of a target cell such as, e.g., spatiotemporal shifts in the expression pattern of genes or of methylation patterns, or the morphological changes leading to changes in aggregation behaviour. The iPS cells can further be subject to studies relating to, e.g., gene therapy, gene targeting, differentiation studies, tests for safety and efficacy of drugs, transplantation of autologous or allogeneic regenerated tissue, tissue repair (e.g., nervous system, heart muscle), diseases like, e.g., Parkinson's disease, heart attack, diabetes, cancer, leukemia or spinal cord injury, embryonal gene expression, genetic manipulation of embryonal genes, early embryology and fetal development, identification of embryonic cell markers, cell migration or apoptosis.

The Figures Show:

FIG. 1: Generation of 2F Oct4/Klf4 (OK) iPS cells from adult NSCs of OG2/Rosa26 transgenic mice.

a. RT-PCR and qRT-PCR analyses of Oct4, Nanog, Klf4, Sox2, and c-Myc in ESCs and NSCs. β-actin was used as loading control. b. Western blot analyses of the four factors in ESCs and NSCs. Anti-actin antibody was used as loading control. c. Morphology of 2F OK iPS cell colony on day 14 post-infection. An ESC-like colony expressing Oct4-GFP (f). d. Morphology of an established 2F OK iPS cells (clone F-4) on day 30 post-infection, grown on irradiated MEFs. Phase contrast and Oct4-GFP (g) are shown. e. Morphology of NSCs and mock infection on day 30 post-infection (h). i. Generation of GFP-positive colonies at day 7, 14, and 21 after 2F OK and 4F infection (n=3; error bars indicated s.d.). j. Reprogramming efficiency of generating 2F and 4F iPS cells (n=3). Indicated are the total numbers of GFP+ colonies per 50,000 plated NSCs at day 7, 14, and 21 after infection.

Figure 2:
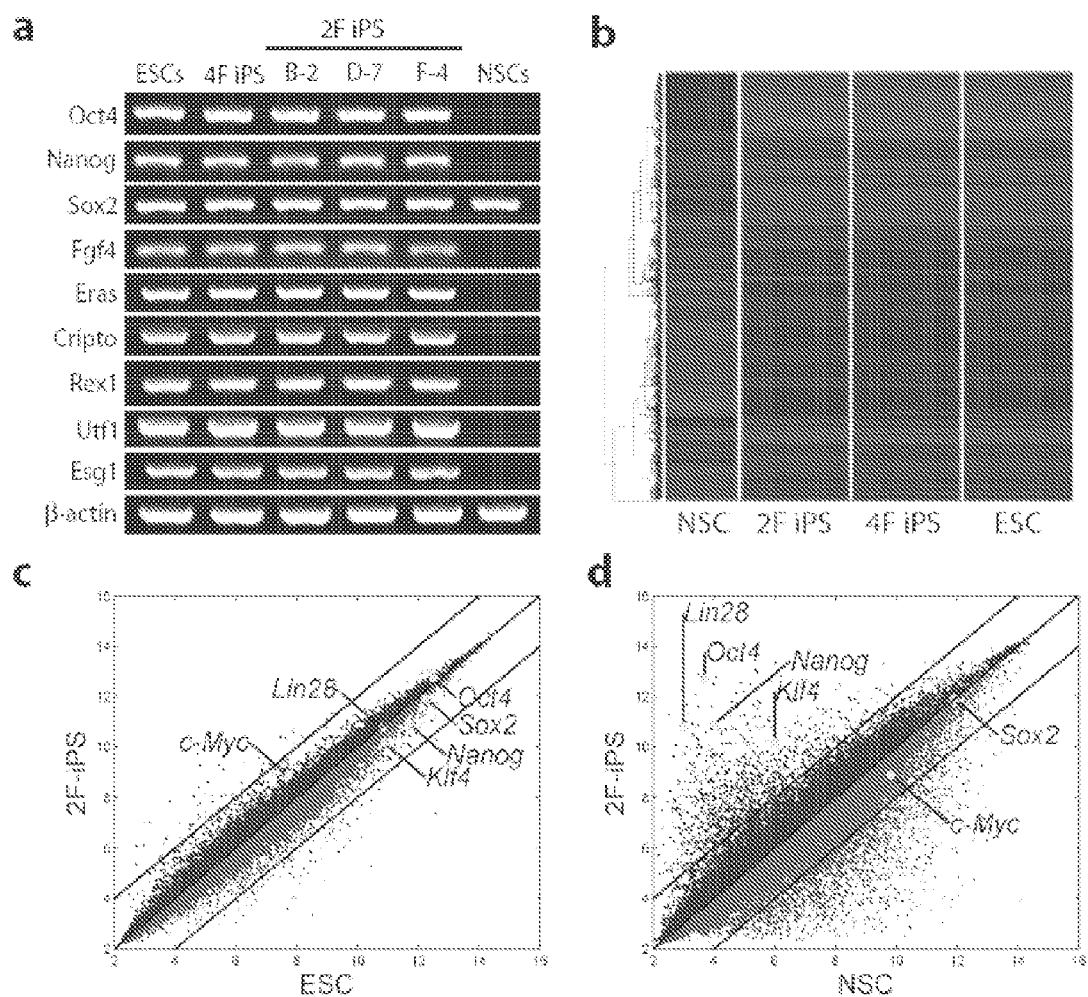

FIG. 2: Gene expression profile of iPS cells.

a. RT-PCR analysis of ES cell marker gene expression in ESCs, 4F iPS cells (clone A-2c), 2F OK iPS cells (clones B-2, D-7 and F-4), and NSCs. Primers are specific for transcripts from the respective endogenous locus. β-actin was used as loading control. b. The heatmap of the different expressed genes among the NSC, 2F (OK) iPS, 4F iPS and ESC. The gene hierarchical cluster was performed with a cityblock distance and an average linkage. c. Global gene expression patterns were compared between 2F iPS cells (clone F-4) and ESCs, and between 2F iPS cells (clone F-4) and NSCs with DNA microarrays. d. Black lines indicate two-fold changes in gene expression levels between the paired cell types. Genes overexpressed in 2F iPS cells (clone F-4) compared with NSCs or ESCs are shown in blue; those underexpressed are shown in red. Positions of pluripotency genes Oct4, Nanog, Sox2, c-Myc, Klf4 and Lin28 in scatter plots are indicated. The gene expression level is scaled in log 2.

Figure 3:
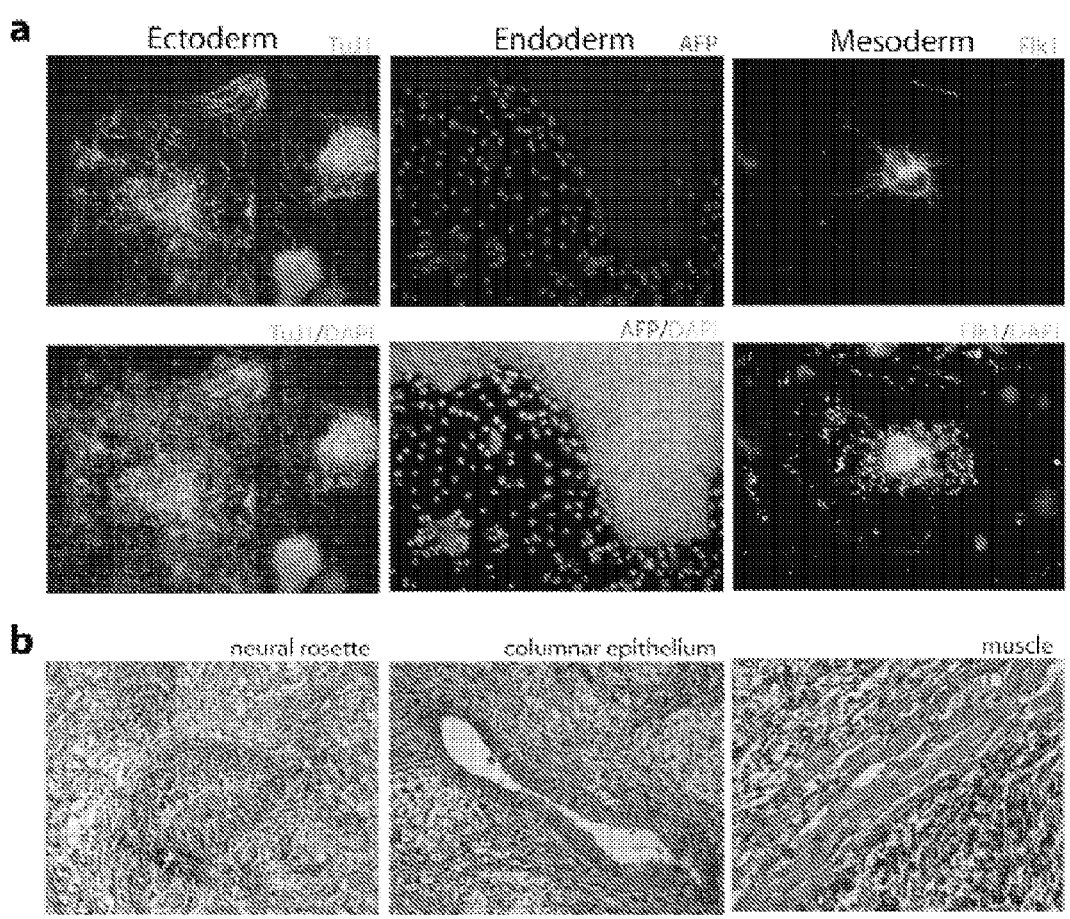

FIG. 3: 2F Oct4/Klf4 (OK) iPS cells (clone F-4) are pluripotent and differentiate in vitro and in vivo.

a. In vitro differentiation into all three germ layers. After embryoid body formation, aggregates were transferred onto gelatine-coated plates and allowed to differentiate for another 10 days. Cells were stained with anti-Tuj1, anti-α-fetoprotein (AFP), or anti-Flk1. Nuclei were stained with DAPI. b. Teratomas of F-4 iPS cells containing all three germ layers. F-4 iPS cells ($1.5 \times 10^6$ cells) were subcutaneously inoculated into nude mice. After 4 weeks, teratomas were stained with haematoxylin and eosin dyes. Shown is a teratoma containing a neural rosette (ectoderm), muscle (mesoderm), and columnar epithelium (endoderm).

Figure 4:
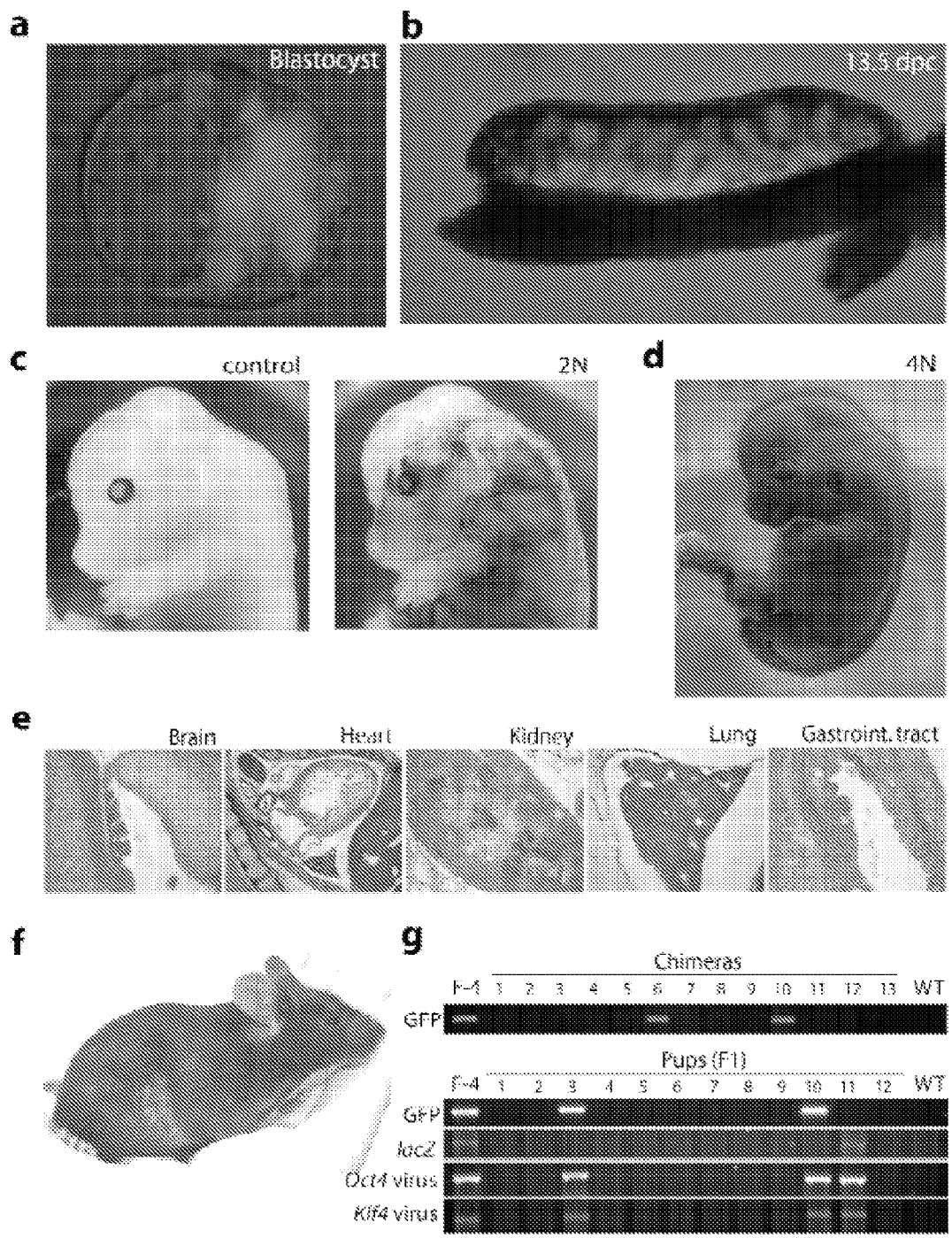

FIG. 4: In vivo developmental potential of 2F Oct4/Klf4 (OK) iPS cells (clone F-4).

a. The chimeric embryos of F-4 iPS cells developed to blastocysts after 24 hrs of aggregation. Fluorescence optics show Oct4-GFP cells located in the inner cell mass of blastocysts. b. Germline contribution of F-4 iPS cells to mouse embryonic development as shown by the expression of Oct4-GFP. Embryos were analyzed with a fluorescence microscope at E13.5. c, d. The 13.5 dpc chimeric embryos (control, 2N, and 4N) were stained with X-gal solution. e. Histological analysis of lacZ-stained 13.5 dpc chimeric embryo (2N). f. Chimeric mouse (8-week-old) generated by F-4 iPS cells. Agouti coat colour originated from F-4 iPS cells. g. PCR genotyping of chimeras derived from F-4 iPS cell. PCR analyses were performed for Oct4-GFP (top panel). Germline transmission of F-4 iPS cells. Genotyping of offspring from chimeric males mated with CD-1 females demonstrated the presence of Oct4-GFP and lacZ allele and Oct4 and Klf4 virus integrations (bottom panel). Abbreviation: Gastroint. tract.: gastrointestinal tract.

Figure 5:
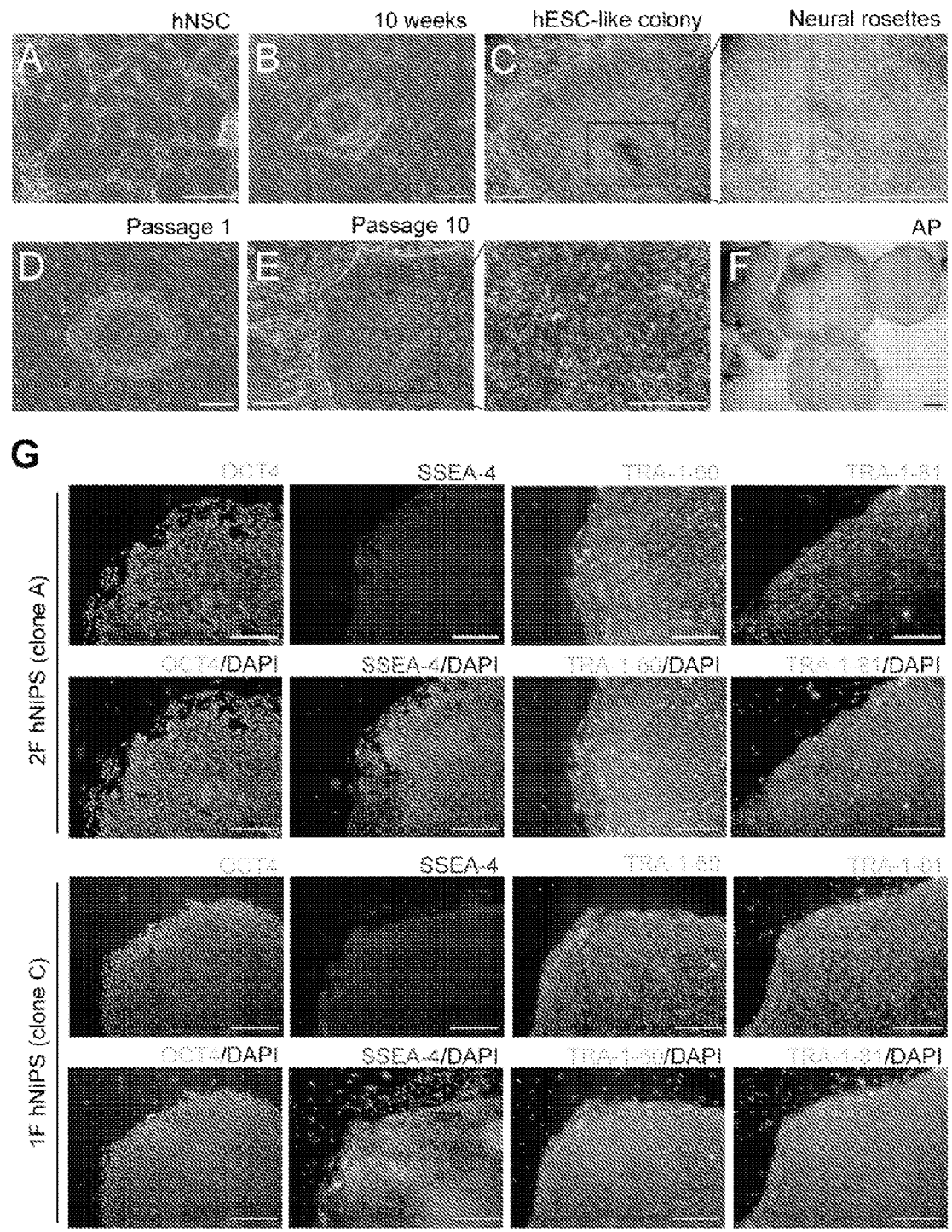

FIG. 5: One-factor hNSC-derived iPS (1F hNiPS) cell colony formation and cell line characterization.

(A) Morphology of hNSCs grown in NSC medium. (B) Colony formation of hOCT4-infected cells 10 weeks post-infection. (C) The colony grows hESC-like morphology but center of colony still remain unreprogrammed neural rosettes. (D) Typical hESC-like iPS colony growing on feeder after mechanical isolation at passage 1 (1 F hNiPS clone C). (E) High magnification of iPS colony at passage 10. (F) 1F hNiPS colonies were stained for AP. Scale bars, 250 µm. (G) Immunocytochemical analysis of pluripotency markers (OCT4, SSEA4, TRA-1-60 and TRA-1-81) in 2F hNiPS (clone A) and 1F hNiPS (clone C) cells. Nuclei are stained with DAPI (blue). Scale bars, 250 µm.

Figure 6:
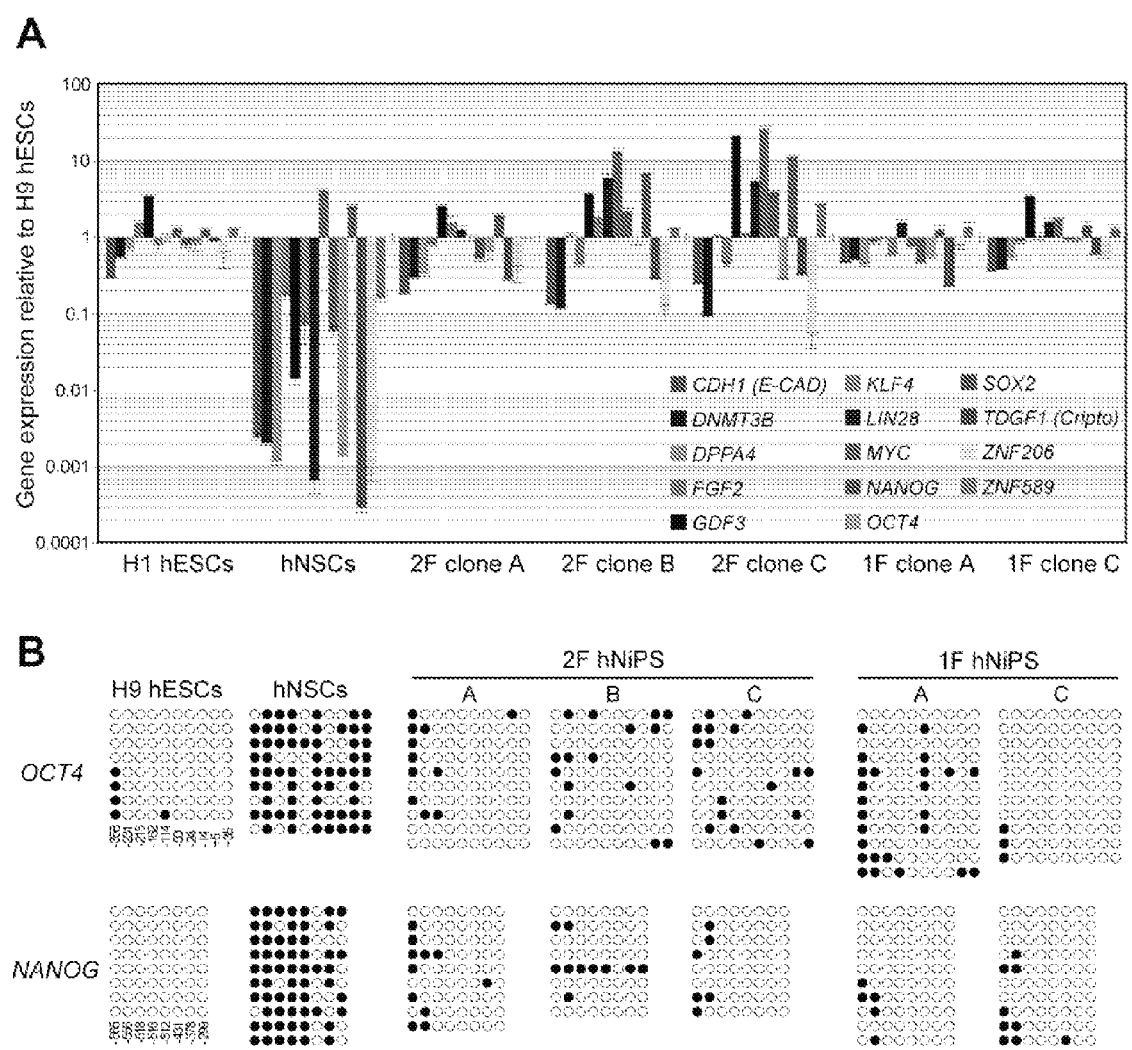

FIG. 6: Expression level of pluripotent markers and DNA methylation analysis in hNSC-derived iPS (hNiPS) cells.

(A) Quantitative PCR analysis for pluripotent markers in H1 hESCs, hNSCs, 2F hNiPS clones (A, B and C) and 1F hNiPS clones (A and C). Data are shown relative expression to H9 hESCs using primers specific for endogenous transcripts. RNA expression levels are shown on logarithmic scale. Transcripts levels were normalized to β-actin levels. Error bars indicate the s.d. from triplicates. (B) Bisulfite sequencing analysis of OCT4 and NANOG promoter regions in H9 hESCs, hNSCs, 2F hNiPS clones (A, B and C) and 1F hNiPS clones (A and C). Each row of circles for a given amplicon represents the methylation status of each CpG in one bacterial clone for that region. Open circles represent unmethylated CpGs, and closed circles represent methylated CpGs. Bottom numbers of each column indicate CpG dinucleotide locations, relative to the transcriptional start site (TSS; +1).

Figure 7:
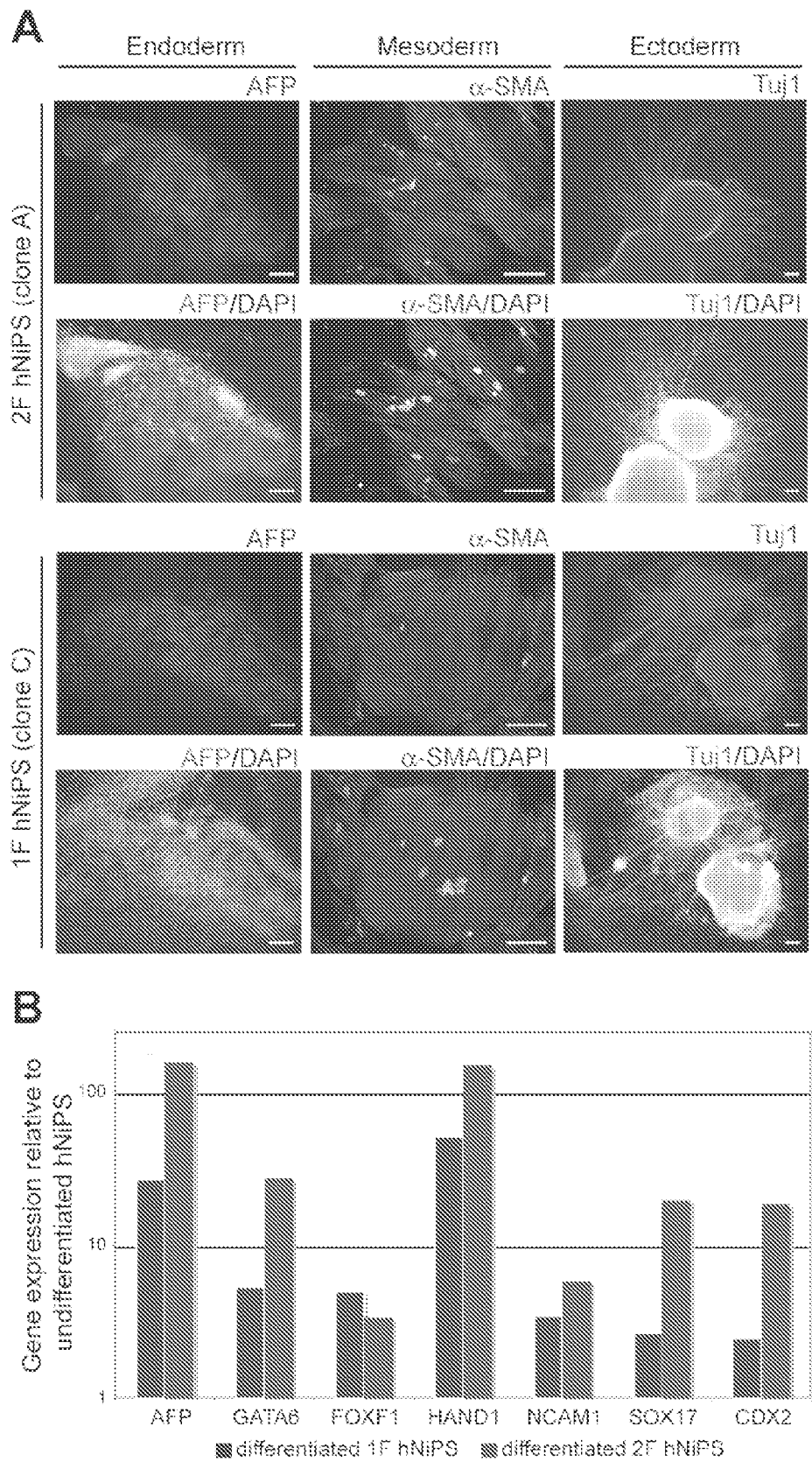

FIG. 7: In vitro differentiation of hNSC-derived iPS (hNiPS) cells into all three germ layers.

(A) Immunofluorescence analysis shows differentiation of 2F and 1F hNiPS cells into all three germ layers: endoderm (alpha-fetoprotein; AFP), mesoderm (alpha-smooth muscle actin; α-SMA) and ectoderm (β-tublin IIIb; Tuj1). Nuclei are stained with DAPI (blue). Scale bars, 100 µm. (B) Quantitative PCR analyses of one-month embryoid bodies (EBs) differentiation derived from 2F hNiPS (clone A) and 1F hNiPS (clone C) cells. Endoderm (AFP, GATA6 and Sox17), mesoderm (FOXF1 and HAND1) and ectoderm (NCAM1, PAX6 and Sox1). Data are shown relative expression to each undifferentiated parental hNiPS cells. RNA expression levels are shown on logarithmic scale. Transcripts levels were normalized to β-actin levels.

FIG. 8: In vivo pluripotency and global gene expression profile of hNSC-derived iPS (hNiPS) cells.

(A) Teratoma formation after transplantation of 2F hNiPS (clone A) and 1F hNiPS (clone C) cells into SCID mice, and teratomas were sectioned and stained with hematoxylin and eosin at 6-8 weeks. Histological section of identified cells representing all three germ layers: endoderm (respiratory epithelium; r), mesoderm (skeletal muscle; m, cartilage; c) and ectoderm (neural epithelium; n). Enlargements of sections showing respiratory epithelium, muscle and neural epithelium indicated by arrows. Scale bars, 100 µm. (B) Heat map (left panel) and hierarchical cluster analysis (right panel) of global gene expression from hNSCs, 1F hNiPS (clone C), 2F hNiPS (clone A) H9 hESCs and H1 hESCs (left). (C) Scatter plots comparing global gene expression profiles between 1F hNiPS (clone C) and H9 hESCs (left panel), 2F hNiPS (clone A) and H9 hESCs (middle panel), and hNSCs and 1F hNiPS (clone C) (right panel). The black lines indicate twofold difference in gene expression levels between the paired cell populations. The transcript expression levels are on the $\log^2$ scale.

The Examples Illustrate the Invention:

EXAMPLE 1

Generation of OG2 Mice

The OG2 strain was crossed with the ROSA26 transgenic strain (Do, J. T. & Scholer, H. R., Stem Cells 22, 941-9 (2004); Szabo, P. E., Hubner, K., Scholer, H. & Mann, J. R., Mech Dev 115, 157-60 (2002)) over several generations to produce compound homozygous mice for the neo/lacZ and Oct4-GFP transgenes. To derive NSCs, homozygous OG2× ROSA26 male mice were crossed with ICR females to produce heterozygous pups. Brain tissue was collected from 5-day-old OG2×ROSA26 heterozygous mice.

EXAMPLE 2

Generation of Induced Pluripotent Stem Cells iPS cells and ESCs were grown on irradiated MEFs and in ESC medium (DMEM supplemented with 15% FBS, nonessential amino acids, L-glutamine, penicillin/streptomycin, β-mercaptoethanol, and 1,000 U/ml leukemia inhibitory factor (LIF)). pMX-based retroviral vectors encoding the mouse cDNAs of Oct4, Sox2, Klf4, and c-Myc were separately cotransfected with packaging-defective helper plasmids into 293 cells using Fugene 6 transfection reagent (Roche). 48 hrs later, virus supernatants were collected as previously described (Zaehres, H. & Daley, G. Q., (2006), Methods Enzymol 420, 49-64). NSCs derived from OG2/ Rosa26 transgenic mice were seeded at a density of $5 \times 10^4$ cells per 6-well plate and incubated with virus-containing supernatants for the four factors (1:1:1:1) or for Oct4 and Klf4 (1:1) supplemented with 6 µg/ml protamine sulfate (Sigma) for 24 hrs. Transduction efficiencies were calculated with pMX-GFP control virus. Cells were replated in fresh neural expansion medium. Two days after infection, the cells were further subcultured on irradiated MEFs in ESC medium containing LIF without any further selection. Oct4-GFP—positive colonies were mechanically isolated, and individual cells were dissociated and subsequently replated onto MEFs. The colonies were selected for expansion.

EXAMPLE 3 qRT-PCR Analysis

Total RNA was extracted from cells using the MiniRNeasy Kit (Qiagen GmbH, Hilden, Germany; http://www.qiagen.com) according to the manufacturer's instructions. Complementary DNA synthesis was performed with the High Capacity cDNA Archive Kit (Applied Biosystems GmbH, Darmstadt, Germany; http://www.appliedbiosystems.com) following the manufacturer's instructions with a down-scaled reaction volume of 20 µl. Transcript levels were determined using the ABI PRISM Sequence Detection System 7900 (Applied BioSystems) and the ready-to-use 5'-nuclease Assays-on-Demand. For each real-time amplification, the template was equivalent to 5 ng of total RNA. Measurements were done in triplicate; a RT⁻ blank of each sample and a no-template blank served as negative controls. Amplification curves and gene expression were normalized to the housekeeping gene Hprt, used as internal standard.

Oligonucleotides were designed by the Taqman Assay-on-Demand for the detection of the following genes: Pou5f1 (Oct3/4) (Mm00658129_gH), Sox2 (Mm00488369_s1), c-Myc (Mm00487803_m1), Klf4 (Mm00516104_m1) B-Act (Mm00607939_s1), and Hprt1 (Mm00446968_m1). Oligos for the detection of Nanog and the viral sequences were custom-designed. Quantification was normalized on the endogenous Hprt gene within the log-linear phase of the amplification curve obtained for each probe/primers set using the ΔΔCt method (ABI PRISM 7700 Sequence Detection System, user bulletin #2).

```
Primer sequences for viral-specific qRT-PCR
pMXs-Oct4 PF:
                                     (SEQ ID NO: 17)
5'-TGGTACGGGAAATCACAAGTTTG, PR:
                                     (SEQ ID NO: 18)
5'-GTCATAGTTCCTGTTGGTGAAGTTCA, Probe:
                                     (SEQ ID NO: 19)
5'-6FAM-CTTCACCATGCCCCTCA-MGB pMXs-Sox2 PF:
                                     (SEQ ID NO: 20)
5'-GTGTGGTGGTACGGGAAATCAC, PR:
                                     (SEQ ID NO: 21)
5'-TTCAGCTCCGTCTCCATCATG, Probe:
                                     (SEQ ID NO: 22)
5'-6FAM-TGTACAAAAAAGCAGGCTTGT-MGB pMXs-Klf4 PF:
                                     (SEQ ID NO: 23)
5'-GTGTGGTGGTACGGGAAATCA,

PR:
                                     (SEQ ID NO: 24)
5'-CGCGAACGTGGAGAAGGA,

Probe:
                                     (SEQ ID NO: 25)
5'-6FAM-CTTCACCATGGCTGTCAG-MGB -continued
pMXs-cMyc PF:
                                     (SEQ ID NO: 26)
5'-TGGTACGGGAAATCACAAGTTTG, PR:
                                     (SEQ ID NO: 27)
5'-GTCATAGTTCCTGTTGGTGAAGTTCA, Probe:
                                     (SEQ ID NO: 28)
5'-6FAM-CTTCACCATGCCCCTCA-MGB Nanog PF:
                                     (SEQ ID NO: 29)
5'-AACCAGTGGTTGAATACTAGCAATG, PR:
                                     (SEQ ID NO: 30)
5'-CTGCAATGGAT GCTG GGATACT, Probe:
                                     (SEQ ID NO: 31)
5'-6FAM-TTCAGAAGGGCTCAGCAC-MGB
```

EXAMPLE 4

Microarray Analysis

The microarray study was carried out using Affymetrix Mouse Genome 430 2.0 GeneChip arrays (Affymetrix, Santa Clara, Calif.) essentially as described before (Ruau, D. et al., (2008), Stem Cells). Briefly, total RNA was extracted from cells with RNAeasy kit including DNAse digestion (Qiagen, Hilden, Germany). Biotin-labelled cRNA was obtained from 3 µg of total RNA with the GeneChip One-Cycle labelling kit (Affymetrix). Fifteen micrograms of cRNA were fragmented and hybridized to Affymetrix 430 2.0 GeneChip arrays at 45° C. for 16 hrs. DNA chips were washed, stained and scanned using an Affymetrix Fluidics device and GCS3000 scanner, and the images obtained were analyzed using the GCOS software. The experiment was performed in triplicates for the ESCs and iPS cells and in duplicates for the NSCs. Normalization was calculated with RMA algorithm (Irizarry, R. A. et al., (2003), Nucleic Acids Res 31, e15) implemented in BioConductor.

EXAMPLE 5

In Vitro Differentiation of iPS Cells

Oct4-GFP cells were harvested by FACS analysis and used for in-vitro differentiation in embryoid bodies (EBs), which was performed with hanging drop in ESC medium without LIF. After 3 days, EBs were plated onto gelatine-coated 4-well dishes for another 10 days. The cells were stained with anti-Tuj1 antibody (1:100; Chemicon), anti-α-fetoprotein (AFP) antibody (1:100; R&D Systems), or anti-Flk1 antibody (1:100; R&D Systems).

EXAMPLE 6

Western Blot Analysis, SSEA-1 and AP Staining

Total cell lysates ($2\times10^6$) prepared from the ESC and NSC were subjected to western blot analysis for expression of Oct4 (Santa Cruz), Sox2 (Santa Cruz), Klf4 (Abcam), and c-Myc (Abcam). β-actin expression levels in all the samples were used as loading control (Abcam).

SSEA-1 and alkaline phosphatase (AP) staining was performed with the ES Cell Characterization Kit (Chemicon) according to the manufacturer's protocol.

EXAMPLE 7

Teratoma Formation iPS cells and NSCs cells ($1.5\times10^6$ cells/mice) were injected subcutaneously into the dorsal flank of nude mice. Four weeks after the injection, teratomas that had formed were fixed overnight in 4% PFA and embedded in paraffin. Sections were stained with haematoxylin and eosin dyes.

EXAMPLE 8

Chimera Formation iPS cells were aggregated and cultured with denuded post-compacted 8-cell-stage mouse embryos. Briefly, 2-cell-stage embryos were flushed from mice [(C57BL/6×C3H) F1 females×CD1 males] at 1.5 dpc and placed in M2 medium and cultured overnight in KSOM medium with 0.1% BSA overnight to 8-cell stage. Clumps of loosely connected iPS cells (10-20 cells) from short trypsin-treated day-2 cultures were selected and transferred into microdrops of KSOM medium with 10% FCS under mineral oil; each clump was placed in a depression in the microdrop. Meanwhile, batches of 30 to 40 embryos were briefly incubated with acidified Tyrode's solution until the zona pellucida had disintegrated. A single embryo was place onto the clump. All aggregates were assembled in this manner, and cultured at 37° C. in an atmosphere of 5% $CO_2$ in air. After 24 hours of culture, the majority of the aggregates had formed blastocysts. A total of 64 aggregated blastocysts (2.5 dpc) were transferred into the uterine horns of five pseudopregnant mice (CD-1 background).

EXAMPLE 9

Reprogramming of Human Neural Stem Cells by Oct4 hNSCs that derived from human fetal brain tissue were expanded in serum-free NSC medium as described previously (cf. FIG. 5A) (Kim et al., Exp Neurol 199, 222 (2006); Park et al., Nat Biotechnol 20, 1111 (2002)). hNSCs were first infected with pMXs encoding human OCT4 and KLF4 (2F) or OCT4 (1F). Then, infected hNSCs were maintained in NSC medium (Kim et al., Exp Neurol 199, 222 (2006)) for up to 7 days. Day 8 post-infection, the cells were replated onto feeder cell layers in hESC medium containing 10 ng/ml bFGF and MEF-conditioned medium (CM) in a 1:1 ratio which culture continued to grow until the hESC-like colonies appeared. Within 10-11 weeks post-infection, the hESC-like iPS colonies were identified but the centre of the colonies still appears like a neural rosette (cf. FIG. 5B). The colony grew larger exhibiting typical hESC-like morphology within another 5-6 days but still the neural rosettes remain in the center of the colony (cf. FIG. 5C). The neural rosettes are removed from the colony. Then, a piece of the colony was transferred on a feeder cell layer by mechanical isolation (cf. FIG. 5D). We successfully established two clones out of three hESC-like colonies by picking from OCT4 infected hNSCs (1F hNiPS clone A and C, reprogramming efficiency 0.02%). Otherwise, we also established 3 clones out of five hESC-like colonies in 2F-infected hNSCs (2F hNiPS A, B and C, reprogramming efficiency, 0.15%) within 7-8 weeks post-infection. All of which could be expanded in hESC culture condition. The 1F hNiPS cells were morphologically similar to hESCs and stained positive for alkaline phosphatase (cf. FIGS. 5E and F). Immunofluorescence staining confirmed that 2F and 1F hNiPS cells uniformly expressed the pluripotency markers, including OCT4, SSEA4, TRA-1-60 and TRA-1-81 (cf. FIG. 5G). These results demonstrate that human iPS cells can be generated from hNSCs by OCT4 and KLF4 as well as OCT4 alone.

Next, we tested mRNA expression levels of pluripotency marker genes in these iPS cells at molecular level by quantitative RT-PCR analysis. 2F and 1F hNiPS cells endogenously expressed the hESCs-specific markers, were similar to H9 and H1 hESCs and were markedly up-regulated compared with parental hNSCs (cf. FIG. 6A). Genotyping PCR showed 1F hNiPS clones have an OCT4 transgene only and 2F hNiPS clones have OCT4 and KLF4 transgenes in the genome. We also confirmed that the expression level of transgenic OCT4 or KLF4 was significantly silenced in 2F and 1F hNiPS clones, except the OCT4 expression from 2F hNiPS clone B. Southern blot analysis confirmed the integration of the OCT4 transgene in 2F and 1F hNiPS clones. To exclude the possibility that iPS clones arose through contamination from hESCs in the laboratory, DNA fingerprinting analysis was performed and confirmed that hNiPS cells precisely correlate to the donor hNSCs (cf. Table 2).

To confirm epigenetic remodelling of the OCT4 and NANOG promoters from reprogrammed cells, we performed bisulfite sequencing to determine the demethylation of both promoters. OCT4 and NANOG promoter regions were demethylatd in 2F and 1F hNiPS cells relative to the donor hNSCs and were similar to hESCs. Taken together, hNSCs can be reprogrammed into iPS cells that similar to hESCs at molecular level by transduction of OCT4 alone.

Next, we tested in vitro pluripotency of 2F and 1F hNiPS cells by embryoid body (EB) differentiation and direct differentiation. hNiPS cells readily differentiated into endoderm (AFP), medoderm (a-SMA) and ectoderm (Tuj1) by EB differentiation (cf. FIG. 5A) and we confirmed the expression of all three germ layer makers from direct differentiation by quantitative RT-PCR analysis (cf. FIG. 7B). To confirm in vivo pluripotency of these human iPS cells, the cells were subcutaneously transplanted into severe combined immunodeficient (SCID) mice. After 6-8 weeks injection, 2F and 1F hNiPS cells gave rise to teratomas containing all three germ layers, including respiratory tract, skeletal muscle, cartilage and neural epithelium (cf. FIG. 8A). These results indicate that 2F and 1F hNiPS cells have a pluripotency in vitro and in vivo alike hESCs.

Finally, we performed global gene expression analysis on hNSC, 2F and 1F hNiPS cells derived from hNSCs, H9 and H1 hESCs by cDNA microarrays. Heat map showed that 2F and 1F hNiPS cells similar to hESCs, otherwise parental hNSCs are isolated from pluripotent polulations (cf. FIG. 8B, left panel) and hierarchical clustering analysis showed that hNiPS cells clustered with hESCs and were distinct from parental hNSCs (cf. FIG. 8B, right panel). Scatter plots analysis showed that hNiPS cells are significantly more similar to hESCs as like between different hESCs than parental hNSCs (cf. FIG. 8C). 1F and 2F hNiPS cells also show similarity with H1 hESCs. These data indicate that hNiPS cells are similar to hESCs in global gene expression profiles. Our results demonstrated 1F and 2F hNiPS cells closely resemble hESCs in molecular level and pluripotency.

TABLE 2

STR analysis of hNSCs and hNiPS cells

| Genomic loci | H9 hESCs | hNSCs | 2F NhiPS A | 2F NhiPS B | 2F NhiPS C | 1F NhiPS A | 1F NhiPS C |
|---|---|---|---|---|---|---|---|
| Amelogenin | X; X | X; Y | X; Y | X; Y | X; Y | X; Y | X; Y |
| CSF1PO | 11; 11 | 11; 13 | 11; 13 | 11; 13 | 11; 13 | 11; 13 | 11; 13 |
| D13S317 | 9; 9 | 8; 11 | 8; 11 | 8; 11 | 8; 11 | 8; 11 | 8; 11 |
| D16S539 | 12; 13 | 9; 9 | 9; 9 | 9; 9 | 9; 9 | 9; 9 | 9; 9 |
| D18S51 | 13; 13 | 15; 16 | 15; 16 | 15; 16 | 15; 16 | 15; 16 | 15; 16 |
| D21S11 | 30; 30 | 31; 32 | 31; 32 | 31; 32 | 31; 32 | 31; 32 | 31; 32 |
| D3S1358 | 13; 16 | 16; 16 | 16; 16 | 16; 16 | 16; 16 | 16; 16 | 16; 16 |
| D5S818 | 11; 12 | 7; 12 | 7; 12 | 7; 12 | 7; 12 | 7; 12 | 7; 12 |
| D7S820 | 9; 11 | 11; 11 | 11; 11 | 11; 11 | 11; 11 | 11; 11 | 11; 11 |
| D8S1179 | 8; 14 | 12; 14 | 12; 14 | 12; 14 | 12; 14 | 12; 14 | 12; 14 |
| FGA | 26; 28 | 23; 24 | 23; 24 | 23; 24 | 23; 24 | 23; 24 | 23; 24 |
| Penta D | 9; 13 | 11; 12 | 11; 12 | 11; 12 | 11; 12 | 11; 12 | 11; 12 |
| Penta E | 11; 14 | 11; 18 | 11; 18 | 11; 18 | 11; 18 | 11; 18 | 11; 18 |
| TH01 | 9; 9 | 7; 7 | 7; 7 | 7; 7 | 7; 7 | 7; 7 | 7; 7 |
| TPOX | 10; 11 | 8; 8 | 8; 8 | 8; 8 | 8; 8 | 8; 8 | 8; 8 |
| vWA | 17; 17 | 17; 17 | 17; 17 | 17; 17 | 17; 17 | 17; 17 | 17; 17 |

Material and Methods:
Cell Culture

Human NSCs were derived from the telencephalon (HFT13), established as previously described (Kim et al., Exp Neurol 199, 222 (2006)). Briefly, Telencephalon tissue was freshly dissected, dissociated in 0.1% trypsin for 30 min and seeded into 10 cm plates at a density of 200,000 cells/ml in NSC medium. These cells were cultured in NSC medium as previously described (Kim et al., Exp Neurol 199, 222 (2006); Park et al., Nat Biotechnol 20, 1111 (2002)). Human ES and iPS cells were maintained on mitomycin C-treated CF1 mouse feeder layers (Millipore) in human ESC medium, which contains knockout DMEM (Invitrogen) supplemented with 20% knockout serum replacement (Invitrogen), 1 mM L-glutamine, 1% non-essential amino acids, 0.1 mM β-mercaptoethanol, penicillin/streptomycin and 10 ng/ml human basic fibroblast growth factor (bFGF) (Invitrogen) as previously described (Takahashi et al., Cell 131, 861 (2007)).

Induction of 1F hNiPS and 2F hNiPs Cells

The pMX-based retroviral vectors encoding the human cDNAs of OCT4 and KLF4 (Takahashi et Yamanaka, Cell 126, 663 (2006)) were cotransfected with packaging-defective helper plasmids into 293 cells using Fugene transfection reagent (Roche) to produce vesicular stomatitis virus (VSV) G protein pseudotyped virus as previously described (Zaehres et Daley, Methods Enzymol 420, 49 (2006)). Viral supernatants were collected and concentrated by ultracentrifugation 48 h post-transfection to infect human NSCs. For generation of iPS cells, human NSCs were seeded at a density of $5 \times 10^4$ cells per 6-well plate and incubated with virus-containing supernatants for OCT4 or OCT4 and KLF4 supplemented with 6 μg/ml protamine sulfate (Sigma) for 24 h. On the next day, the medium was replaced with fresh NSC medium at 1d post-infection and maintained up to 7 d post-infection. Cells were further cultured in human ESC medium from 8 d post-infection. The iPS colonies were mechanically isolated at 2 month or 2.5 month post-infection and were subsequently replated and maintained on CF1 mouse feeder layers (Millipore) in human ESC medium.

Quantitative RT-PCR

Total RNA was isolated from bulk cell culture samples or hand-picked undifferentiated colonies using RNeasy columns (Qiagen) with on-column DNA digestion. cDNA was produced using oligo-dT$_{15}$ priming and M-MLV reverse transcriptase (USB) according to the manufacturer's instructions at 42° C. for 1 h. About 50 ng of total RNA equivalent was typically used as template in 20 μl SYBR Green PCR reactions (40 cycles of 15" 95° C./60" 60° C. on Applied Biosystems 7300 instrumentation) that additionally contained 0.375 μM of each primer and 10 μl of SYBR Green PCR mix (ABI). All primers used were confirmed to amplify the predicted product at close-to-optimal efficiency without side products. Primer sequences are given in Table 3. Relative expression levels were calculated using the comparative Ct method, based on biological control samples and two housekeeping genes for normalization. Error bars reflect standard errors arising from biological replicates (marker gene expression data) or from using independent housekeeping genes for normalization (transgene silencing data).

Global Gene Expression Analysis

For transcriptional analysis, 400 ng of total DNA-free RNA was used as input for labelled cRNA synthesis (Illumina TotalPrep RNA Amplification Kit—Ambion) following the manufacturer's instructions (IVT: 10 h). Quality-checked cRNA samples were hybridized as biological or technical duplicates for 18 h onto HumanRef-8 v3 expression BeadChips (Illumina), washed, stained, and scanned following guidelines and using materials/instrumentation supplied/suggested by the manufacturer. The microarray data are available from the GEO (Gene Expression Omnibus) website under accession number GSE GSE15355.

Bisulfite Sequencing

Genomic DNA was isolated from bulk cell culture samples or hand-picked undifferentiated colonies using DNeasy columns (Qiagen). 300 ng was used as input for bisulfite conversion (EpiTect Bisulfite Kit—Qiagen). 50 ng of converted DNA was used as template for conventional nested PCRs amplifying 467 and 336 bp regions of the OCT4 and NANOG promoters, respectively. Primers were specific for conversion of the sense DNA strand and are given in Table 3. Purified PCRs were TA-cloned into pCR2.1-TOPO (Invitrogen). Insert sequences of randomly picked clones were analyzed using the BiQ Analyzer program, following its quality check-based suggestions to drop individual clones if appropriate. Data from one CpG site at position +20 relative to the OCT4 translation start codon is not shown as it was uninformative.

Short Tandem Repeat (STR) Analysis

Genomic DNA was isolated from cultured cell samples using DNeasy columns (Qiagen). This was used as template for STR analysis employing the PowerPlex 16 System (Promega) and ABI PRISM instrumentation. Numbers shown denote by lengths of the 15 autosomal fragments. The analysis was carried out at Eurofins Medigenomix, Martinsried, Germany.

Teratoma Formation hNiPS cells and hNSCs (3-5×10$^6$ cells/mice) were injected subcutaneously into the dorsal flank of SCID mice. Teratomas were fixed in 4% PFA overnight and embedded in paraffin after 6-8 weeks injection. Sections were stained with haematoxylin and eosin dyes.

Alkaline Phosphatase (AP) and Immunofluorescence Staining

Alkaline phosphatase (AP) staining was performed with the ES Cell Characterization Kit (Chemicon) according to the manufacturer's protocol. Immunofluorescence staining was performed using the following primary antibodies: AFP (Sigma, 1:100), a-SMA (Sigma, 1:50), TuJ1 (Chemicon, 1:500), OCT4 (Santa Cruz, 1:200), SSEA4 (Chemicon, 1:200), TRA-1-60 (Chemicon, 1:200), TRA-1-81 (Chemicon, 1:200).

TABLE 3

Primers for Real-time PCR and Bisulfite sequencing.

| Gene | Forward primer (5'-3') | Reverse primer (5'-3') |
|---|---|---|
| Real-time PCR Primers | | |
| ACTB | TCAAGATCATTGCTCCTCCTGAG | ACATCTGCTGGAAGGTGGACA |
| AFP | AGCAGCTTGGTGGTGGATGA | CCTGAGCTTGGCACAGATCCT |
| CDH1 (E-CAD) | TTGAGGCCAAGCAGCAGTACA | ATCCAGCACATCCACGGTGA |
| CDX2 | TCACTACAGTCGCTACATCACCATC | TTAACCTGCCTCTCAGAGAGCC |
| DNMT3B | GCTCACAGGGCCCGATACTT | GCAGTCCTGCAGCTCGAGTTTA |
| DPPA4 | TGGTGTCAGGTGGTGTGTGG | CCAGGCTTGACCAGCATGAA |
| FGF2 | GGCAAGATGCAGGAGAGAGGA | GCCACGTGAGAGCAGAGCAT |
| FOXF1 | AAAGGAGCCACGAAGCAAGC | AGGCTGAAGCGAAGGAAGAGG |
| GAPDH | CTGGTAAAGTGGATATTGTTGCCAT | TGGAATCATATTGGAACATGTAAACC |
| GATA6 | TGTGCGTTCATGGAGAAGATCA | TTTGATAAGAGACCTCATGAACCGACT |
| GDF3 | TTGGCACAAGTGGATCATTGC | TTGGCACAAGTGGATCATTGC |
| HAND1 | TCCCTTTTCCGCTTGCTCTC | CATCGCCTACCTGATGGACG |
| KLF4 endo | ACAGTCTGTTATGCACTGTGGTTTCA | CATTTGTTCTGCTTAAGGCATACTTGG |
| KLF4 viral | GTCGGACCACCTCGCCTTAC | TTTATCGTCGACCACTGTGCTG |
| LIN28 | GGAGGCCAAGAAAGGGAATATGA | AACAATCTTGTGGCCACTTTGACA |
| MYC | CCAGCAGCGACTCTGAGGA | GAGCCTGCCTCTTTTCCACAG |
| NANOG | CCTGTGATTTGTGGGCCTG | GACAGTCTCCGTGTGAGGCAT |
| NCAM1 | TCATGTGCATTGCGGTCAAC | ACGATGGGCTCCTTGGACTC |
| OCT4 endo | GGAAGGAATTGGGAACACAAAGG | AACTTCACCTTCCCTCCAACCA |
| OCT4 viral | GGCTCTCCCATGCATTCAAAC | TTTATCGTCGACCACTGTGCTG |
| SOX17 | TTCGTGTGCAAGCCTGAGATG | GTCGGACACCACCGAGGAA |
| SOX2 | TGGCGAACCATCTCTGTGGT | CCAACGGTGTCAACCTGCAT |
| TDGF1 (Cripto) | GGGATACAGCACAGTAAGGAGCTAA | CACAAAAGGACCCCAGCATG |
| ZNF206 | TCACCATGGCCAGAGGAGAG | GCAGGCCACGCCTTATTCTC |
| ZNF589 | TCGGGTGGCTAAATTACATCCAG | CCCAAGGGAGTAAGGCAAACTG |
| Primers for bisulfite sequencing | | |
| OCT4 outer | GAGGATAGGAATTTAAGATTAGTTTGGGTA | AAATCCCCACACCTCAAAACCTAACCCAA |
| OCT4 inner | GAGGTTGGAGTAGAAGGATTGTTTTGGTTT | CCCCCCTAACCCATCACCTCCACCACCTAA |
| OCT4 inner unconverted | GAGGCTGGAGCAGAAGGATTGCTTTGGCCC | CCCCCCTGGCCCATCACCTCCACCACCTGG |
| NANOG outer | TTAGTTTTTAGAGTAGTTGGGATTATAGA | ATAATAACATAAAACAACCAACTCAATCCA |

TABLE 3-continued

Primers for Real-time PCR and Bisulfite sequencing.

| Gene | Forward primer (5'-3') | Reverse primer (5'-3') |
|---|---|---|
| NANOG inner | TGGTTAGGTTGGTTTTAAATTTTG | AACCCACCCTTATAAATTCTCAATTA |
| NANOG inner unconverted | TGGCCAGGCTGGTTTCAAACTCCTG | GACCCACCCTTGTGAATTCTCAGTTA |

Southern Blot Analysis

BamHI digested genomic DNA from 1F hNiPS, hNSC and 2F hNiPS cells were separated on a 0.8% agarose gel and transferred to Biodyne B nylon membrane (PALL Life Sciences). DNA was hybridized with a 32P labeled fragment of OCT4 (Eco81I (Saul) human OCT4 cDNA fragment) using the DecaLabel™ DNA Labeling Kit (Fermentas). Labeled Lambda HindIII digested DNA served as a marker.

In Vitro Differentiation of Human iPS Cells

For immunocytochemistry, embryoid bodies (EBs) were generated from iPS cells with the hanging drop method in MEF-conditioned medium. After 5 days, EBs were transferred to gelatin-coated plate and subsequent culturing for another 14 days in knockout DMEM (Invitrogen) supplemented with 20% FBS, 1 mM L-glutamine, 1% non-essential amino acids, 0.1 mM β-mercaptoethanol, and penicillin/streptomycin. For qRT-PCR, iPS colonies were mechanically isolated and replated on Matrigel-coated plate in MEF-conditioned medium. After 2 d, medium replaced with each three germ layer differentiation medium. For endoderm differentiation, the cells maintained in RPMI1640 medium supplemented with 2% FBS, 100 ng/ml Activin A (R&D Systems), L-glutamine, and penicillin/streptomycin for 3 weeks (Huangfu et al., Nat Biotechnol 26, 1269 (2008)). For mesoderm differentiation, knockout DMEM supplemented with 100 uM ascorbic acid (Sigma), 20% FBS, 1 mM L-glutamine, 1% non-essential amino acids, 0.1 mM β-mercaptoethanol, and penicillin/streptomycin for 3 weeks (Aasen et al., Nat Biotechnol 26, 1276 (2008)). For ectoderm differentiation, the cells maintained in N2B27 medium for 7 days and the medium replaced with N2 medium supplemented with 10 ng/ml bFGF2 (peprotech), 100 ng/ml Sonic Hedgehog (R&D Systems), 10 ng/ml PDFG (R&D Systems), L-glutamine, and penicillin/streptomycin for 2 weeks. The medium was changed every other day. Primer sequences are given in Table 3.

REFERENCES

Biswas, A. and Hutchins, R. (2007). Embryonic stem cells. Stem Cells Dev 16(2):213-22.
Davis, P. B., Cooper, M. J. (2007). Vectors for airway gene delivery. AAPS J 19; 9(1):E11-7.
Do, J. T. & Scholer, H. R. (2004). Nuclei of embryonic stem cells reprogram somatic cells. Stem Cells 22:941-9.
Gage, F. H. (2000). Mammalian neural stem cells. Science 287(5457):1433-8.
Hanna, J., Wernig, M., Markoulaki, S., Sun, C. W., Meissner, A., Cassady, J. P., Beard, C., Brambrink, T., Wu, L. C., Townes, T. M. and Jaenisch, R. (2007). Treatment of sickle cell anemia mouse model with iPS cells generated from autologous skin. Science 318(5858):1920-3.
Hogan, B., R. Beddington, et al. (1994), "Manipulating the Mouse Embryo: A Laboratory Manual", Cold Spring Harbour Press.
Jones, G. E., Wise, C. J. (1997). Establishment, maintenance, and cloning of human dermal fibroblasts. Methods Mol Biol. 75:13-21.
Kim, D. S., Kim, J. Y., Kang, M., Cho, M. S., Kim, D. W. (2007). Derivation of functional dopamine neurons from embryonic stem cells. Cell Transplant 16(2):117-23.
Li, S. and Ma, Z. (2001). Nonviral gene therapy. Curr Gene Ther., 1(2):201-26.
Meissner, A., Wernig, M. and Jaenisch, R. (2007). Direct reprogramming of genetically unmodified fibroblasts into pluripotent stem cells. Nat Biotechnol 25(10): 1177-81.
Nakagawa, M., Koyanagi, M., Tanabe, K., Takahashi, K., Ichisaka, T., Aoi, T., Okita, K., Mochiduki, Y., Takizawa, N. and Yamanaka, S. (2008). Generation of induced pluripotent stem cells without Myc from mouse and human fibroblasts. Nat Biotechnol. 26(1):101-6.
Okita, K., Ichisaka, T. and Yamanaka, S. (2007). Generation of germline-competent induced pluripotent stem cells. Nature 448(7151):313-7.
Park, I. H., Zhao, R., West, J. A., Yabuuchi, A., Huo, H., Ince, T. A., Lerou, P. H., Lensch, M. W., Daley, G. Q. (2008). Reprogramming of human somatic cells to pluripotency with defined factors. Nature 451(7175):141-6.
Pollard, S. M., Conti, L., Sun, Y., Goffredo, D. & Smith, A. (2006). Adherent neural stem (NS) cells from fetal and adult forebrain. Cereb Cortex 16 Suppl 1, i112-20.
Ryan, A. K. and Rosenfeld, M. G. (1997). POU domain family values: flexibility, partnerships, and developmental codes. Genes Dev 11:1207-25.
Takahashi, K. and Yamanaka, S. (2006). Induction of pluripotent stem cells from mouse embryonic and adult fibroblast cultures by defined factors. Cell 126:663-76.
Takahashi, K., Okita, K., Nakagawa, M., and Yamanaka, S. (2007). Induction of pluripotent stem cells from fibroblast cultures. Nat Protoc 2(12):3081-9.
Takahashi, K., Tanabe, K., Ohnuki, M., Narita, M., Ichisaka, T., Tomoda, K. and Yamanaka, S. (2007). Induction of pluripotent stem cells from adult human fibroblasts by defined factors. Cell 131(5):861-72.
Wernig, M., Meissner, A., Foreman, R., Brambrink, T., Ku, M., Hochedlinger, K., Bernstein, B. E. and Jaenisch, R. (2007). In vitro reprogramming of fibroblasts into a pluripotent ES-cell-like state. Nature 448:318-24.
Wernig, M., Meissner, A., Cassady, J. P. and Jaenisch, R. (2008). c-Myc is dispensable for direct reprogramming of mouse fibroblasts. Cell Stem Cells 2:10-12.
Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., Slukvin, I. I. and Thomson, J. A. (2007). Induced pluripotent stem cell lines derived from human somatic cells. Science 318(5858):1917-20.
Zimmermann, W. H. and Eschenhagen, T. (2007). Embryonic stem cells for cardiac muscle engineering. Trends Cardiovasc Med 17(4):134-40.
H. T. Kim et al., Exp Neurol 199, 222 (May, 2006)
K. I. Park, Y. D. Teng, E. Y. Snyder, Nat Biotechnol 20, 1111 (November 2002)
H. Zaehres, G. Q. Daley, Methods Enzymol 420, 49 (2006)
D. Huangfu et al., Nat Biotechnol 26, 1269 (November 2008)
T. Aasen et al., Nat Biotechnol 26, 1276 (November 2008)

The invention claimed is:

1. A method of generating an induced pluripotent stem (iPS) cell comprising
  (a) administering to a neural stem cell (NSC)
    (i) a nucleic acid sequence encoding Oct3/4; and (ii) a nucleic acid sequence encoding Klf4, wherein the neural stem cell endogenously expresses Sox2, but does not endogenously express Oct3/4 or Klf4; and
  (b) obtaining an induced pluripotent stem (iPS) cell from step (a), wherein the iPS cell expresses Oct3/4, Klf4 and the endogenously expressed Sox2.

2. The method of claim 1, wherein the neural stem cell is a murine neural stem cell.

* * * * *